(12) United States Patent
Pisharodi

(10) Patent No.: US 11,511,013 B2
(45) Date of Patent: Nov. 29, 2022

(54) AIR PURIFICATION AND DISINFECTION APPARATUS AND METHODS OF USE

(71) Applicant: Madhavan Pisharodi, Brownsville, TX (US)

(72) Inventor: Madhavan Pisharodi, Brownsville, TX (US)

(*) Notice: Subject to any disclaimer, the term of this patent is extended or adjusted under 35 U.S.C. 154(b) by 0 days.

(21) Appl. No.: 17/545,822

(22) Filed: Dec. 8, 2021

(65) Prior Publication Data

US 2022/0096701 A1 Mar. 31, 2022

Related U.S. Application Data

(60) Continuation-in-part of application No. 17/355,169, filed on Jun. 22, 2021, which is a division of
(Continued)

(51) Int. Cl.
*A61L 9/20* (2006.01)
*F24D 15/00* (2022.01)
(Continued)

(52) U.S. Cl.
CPC .............. *A61L 9/20* (2013.01); *A62B 7/02* (2013.01); *A62B 9/00* (2013.01); *A62B 11/00* (2013.01);
(Continued)

(58) Field of Classification Search
CPC .................................. A61L 9/20; A62B 7/10
See application file for complete search history.

(56) References Cited

U.S. PATENT DOCUMENTS

| 4,742,760 A | 5/1988 | Horstman |
| 5,165,395 A | * 11/1992 | Ricci ................. A41D 13/1146 55/DIG. 35 |

(Continued)

FOREIGN PATENT DOCUMENTS

| BG | 3818 | * 7/2020 |
| CN | 111457496 A | * 7/2020 |

OTHER PUBLICATIONS

Document entitled: CN111457496A Portable air purification device and active mask comprising same, machine translation of CN111457496A provided by Espacenet (Year: 2020).*
(Continued)

*Primary Examiner* — Donald R Spamer
(74) *Attorney, Agent, or Firm* — D'Ambrosio & Menon, PLLC; Usha Menon

(57) ABSTRACT

An air purification and disinfection system includes an apparatus having a housing, an ultraviolet disinfection chamber, an air mover, and an air distribution unit in communication with the disinfection chamber. Air is passed through the disinfection chamber where it is purified and disinfected before it is delivered to the user of the apparatus through the air distribution unit. The apparatus can be configured as an open or a closed circuit system. The system may be configured to purify air in an airplane, a conference room, a classroom, or as a portable unit for an individual user. As a portable unit the disinfection chamber can be incorporated into a back pack, a vest, a purse, a briefcase, a shoulder bag, a cervical collar, or any other format for being carried by the user.

37 Claims, 36 Drawing Sheets

Related U.S. Application Data application No. 16/987,011, filed on Aug. 6, 2020, now Pat. No. 11,052,169.

(60) Provisional application No. 63/233,697, filed on Aug. 16, 2021, provisional application No. 63/029,290, filed on May 22, 2020, provisional application No. 63/022,307, filed on May 8, 2020.

(51) Int. Cl.

| | |
|---|---|
| *B01D 46/10* | (2006.01) |
| *B01D 46/00* | (2022.01) |
| *A62B 11/00* | (2006.01) |
| *A62B 23/00* | (2006.01) |
| *A62B 7/02* | (2006.01) |
| *A62B 9/00* | (2006.01) |
| *B64D 13/08* | (2006.01) |
| *B64F 5/30* | (2017.01) |
| *F24F 3/16* | (2021.01) |
| *B64D 13/06* | (2006.01) |
| *F24F 8/22* | (2021.01) |

(52) U.S. Cl.
CPC .......... *A62B 23/00* (2013.01); *B01D 46/0028* (2013.01); *B01D 46/0049* (2013.01); *B01D 46/10* (2013.01); *B64D 13/08* (2013.01); *B64F 5/30* (2017.01); *F24D 15/00* (2013.01); *F24F 3/16* (2013.01); *A61L 2209/12* (2013.01); *A61L 2209/14* (2013.01); *A61L 2209/16* (2013.01); *B01D 2273/26* (2013.01); *B01D 2273/30* (2013.01); *B01D 2279/50* (2013.01); *B01D 2279/65* (2013.01); *B64D 2013/0651* (2013.01); *B64D 2013/0688* (2013.01); *F24F 8/22* (2021.01)

(56) References Cited

U.S. PATENT DOCUMENTS

| | | | |
|---|---|---|---|
| 5,656,242 | A | 8/1997 | Morrow et al. |
| 6,875,988 | B1* | 4/2005 | Sauska .................. B01D 45/12 |
| | | | 250/455.11 |
| 7,185,510 | B2 | 3/2007 | Lee et al. |
| 7,658,891 | B1* | 2/2010 | Barnes .................... C01B 13/11 |
| | | | 128/205.28 |
| 8,336,821 | B2 | 12/2012 | Shell et al. |
| 10,905,791 | B1* | 2/2021 | Caballero ................ A61L 9/20 |
| 2006/0057020 | A1 | 3/2006 | Tufo |
| 2008/0173178 | A1 | 7/2008 | Metteer |
| 2012/0128539 | A1* | 5/2012 | Gross ...................... F24F 8/192 |
| | | | 422/121 |
| 2016/0001108 | A1 | 1/2016 | Zhou et al. |
| 2017/0266335 | A1* | 9/2017 | Al-Zeer ................ A61L 9/205 |
| 2017/0341762 | A1 | 11/2017 | Breigenzer |
| 2018/0250430 | A1 | 9/2018 | Machovina et al. |
| 2019/0009912 | A1 | 1/2019 | Matsui |
| 2019/0167833 | A1* | 6/2019 | Yang ........................ A61L 9/20 |
| 2019/0313785 | A1* | 10/2019 | Jimenez .................... A61L 2/10 |
| 2020/0282086 | A1* | 9/2020 | Silverman ................ A61L 2/10 |
| 2021/0298391 | A1* | 9/2021 | Keene .................... A62B 18/02 |
| 2021/0330850 | A1* | 10/2021 | Catalan .................... F24F 8/22 |
| 2021/0339058 | A1* | 11/2021 | Connor .................. A62B 18/006 |
| 2021/0361818 | A1* | 11/2021 | Almeida ................ A62B 23/02 |
| 2021/0379232 | A1* | 12/2021 | Singal .................... A62B 18/02 |
| 2021/0379234 | A1* | 12/2021 | Li ............................ A61L 9/20 |
| 2022/0001068 | A1* | 1/2022 | Greenspan ................ A61L 9/20 |
| 2022/0054666 | A1* | 2/2022 | Phillips .................. A61L 2/0047 |

OTHER PUBLICATIONS

Document entitled: 3818 U1 Mobile Filter for Respirator Masks With UVC Sources and Electronic Control Unit, machine translation of BG 3818 provided by Google Translate (Year: 2020).*

How a packaged system works (Goodman) Jul. 29, 2016, [online] retrieved from <URL: https://web.archive.org/web/20160729193422/ https://www.goodmanmfg.com/resources/heating-cooling-101/how-a-packaged-system-works>.

* cited by examiner

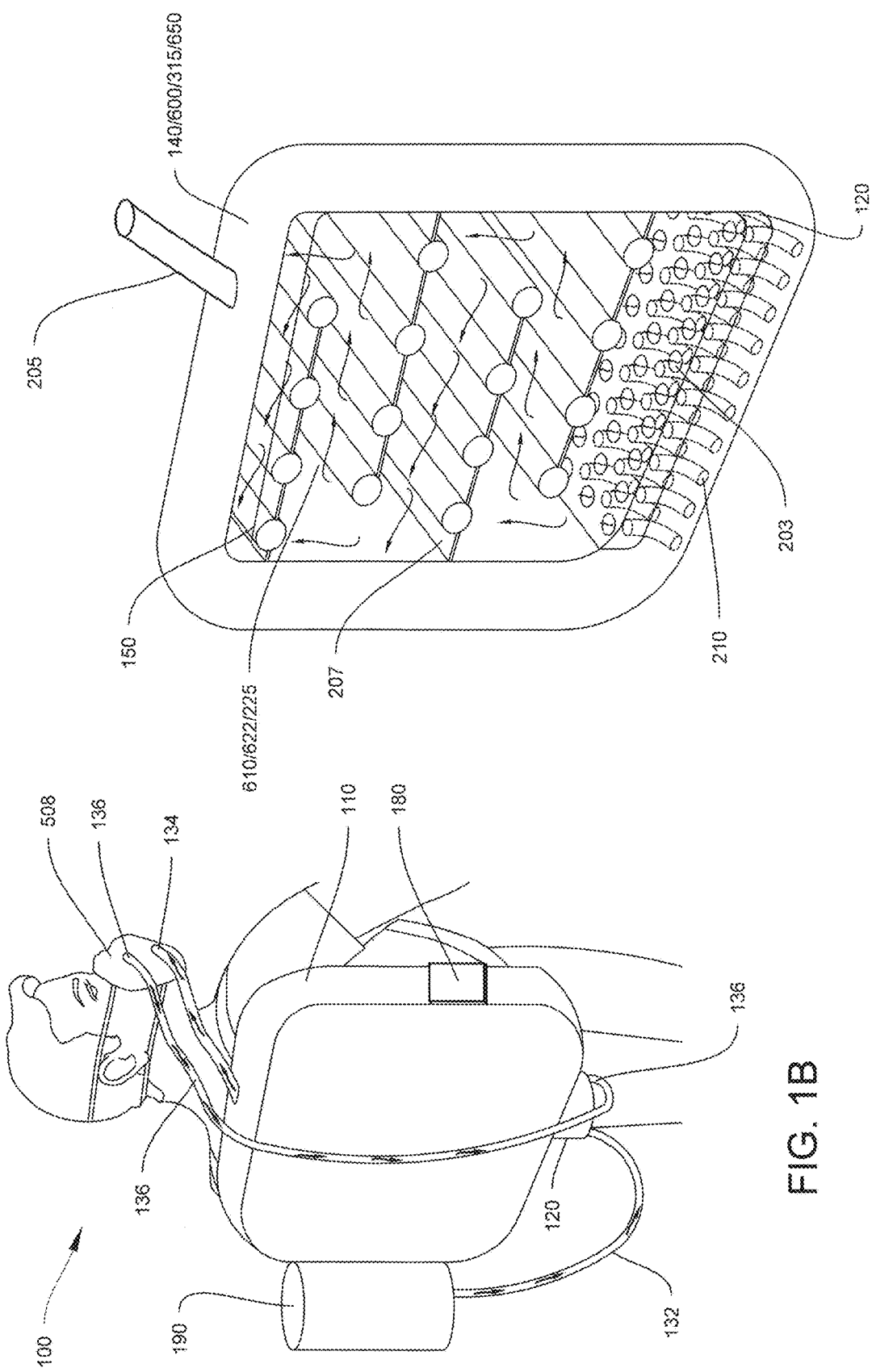

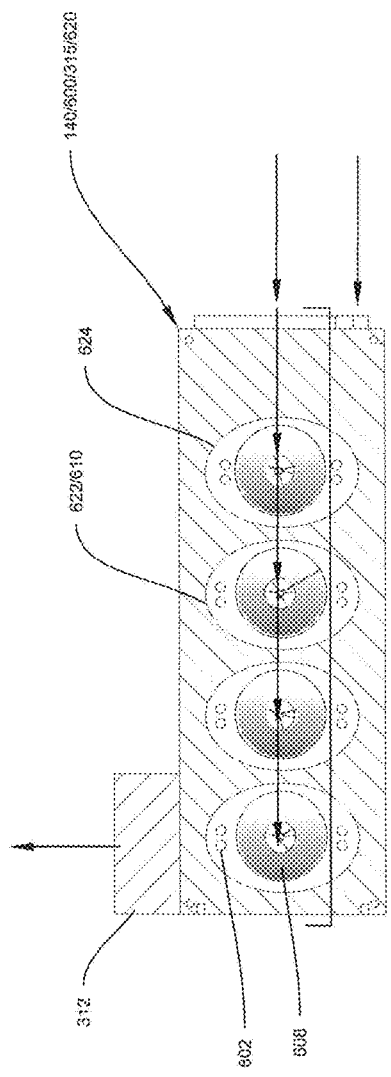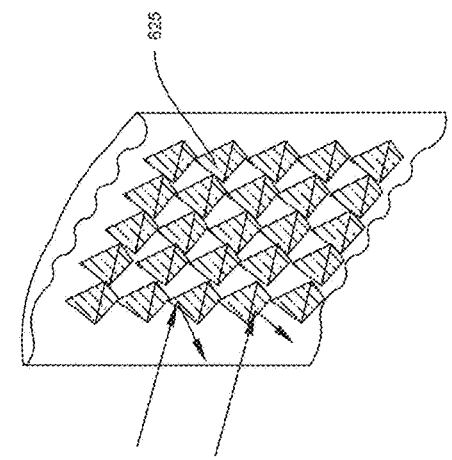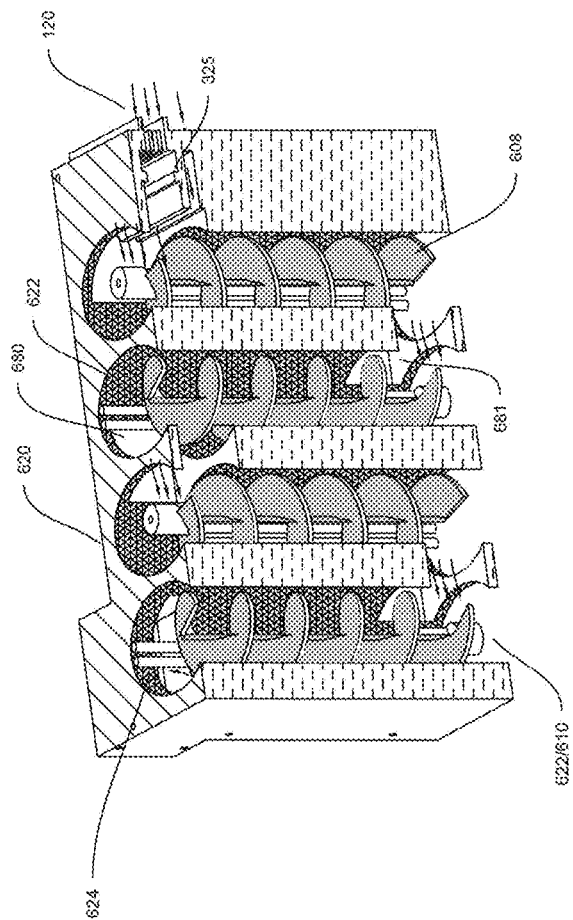
FIG. 6G
FIG. 6I
FIG. 6H

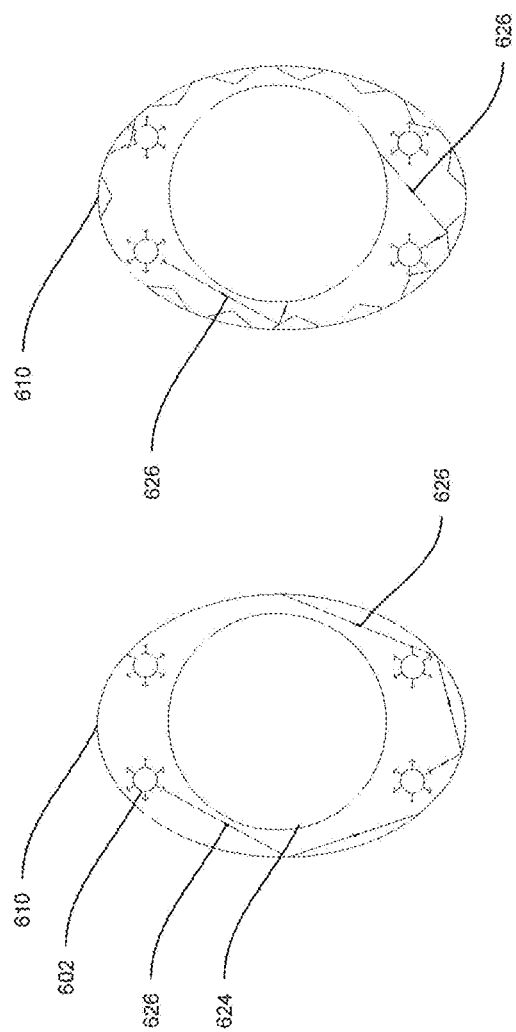

AIR PURIFICATION AND DISINFECTION APPARATUS AND METHODS OF USE

CROSS REFERENCE TO RELATED APPLICATIONS

This application is a non-provisional application of and claims priority to U.S. Ser. No. 63/233,697 filed on Aug. 16, 2021; this application is also a continuation-in-part of U.S. patent application Ser. No. 17/355,169 which is a divisional of and claims priority from U.S. patent application Ser. No. 16/987,011 filed on Aug. 6, 2020 which claims priority to U.S. Provisional Patent Application Ser. No. 63/022,307 filed on May 8, 2020 and U.S. Provisional Patent Application Ser. No. 63/029,290 filed on May 22, 2020, the entire disclosures of which are part of the disclosure of the present application and are hereby incorporated by reference in their entireties.

FIELD OF THE INVENTION

The present invention relates to a personal air purification and disinfection apparatus and methods of its use, and in particular to apparatuses and systems that eliminate harmful airborne particles and microorganisms from ambient air as it passes through the device, so as to prevent the organisms entering the body of an individual user of the apparatus.

BACKGROUND

The background description includes information that may be useful in understanding the present invention. It is not an admission that any of the information provided herein is prior art or relevant to the presently claimed invention, or that any publication specifically or implicitly referenced is prior art.

Social distancing and the use of personal protective equipment (PPE), such as mask and face shields, have been recommended to protect individuals and control spread of airborne viruses, such as, SARS-CoV-2 (or the COVID-19) virus. However, these measures may not be sufficient to contain the spread of the COVID-19 virus especially in confined spaces. Most face masks have questionable ability to block fine virus particles. In infected individuals, the masks block the escape of large virus droplets thus forcing them to breath in more and more viruses with each breath and reinfect themselves with the viruses they should be expelling. Social distancing is of questionable value in a facility where people move around because the virus droplets take eight minutes or more to drop from a height of five feet. Inevitably, a virus "halo" from the infected person lies in wait for the next person to pass by. Lockdowns have only temporary value because the virus is still present in the ambient air when the lockdown is lifted. To be effective, the virus has to be destroyed and the battle should be preferably outside the body since we do not yet know the long-term complications suffered by individuals who are supposedly "cured" of the COVID-19 virus nor the long-term effects of current vaccines. Recent studies have found that the COVID-19 virus and other variants spread not only through close personal contacts but also through the air. Even if the virus droplets fall down within a six-foot radius, the viruses in these droplets are not destroyed. Instead, these droplets dry up, release the virus particles of about 0.1 micron to float into the air converting rooms, buildings, airplanes, etc. into something similar to smoke filled facilities. Even an N95 mask cannot block these particles completely.

For example, the COVID-19 virus can infect buildings, airplanes, buses, trains and other structures that have inadequate disinfection functionality in the associated air conditioning systems or in air conditioners with sluggish air movement. Such air conditioners can function as a "vector equivalent" for the COVID-19 virus and other microorganisms. Individuals in confined/enclosed spaces are constantly exposed to this deadly virus every time they inhale the air from an infected building or structure and the masks may not be able to protect the individuals because either the masks cannot block such fine virus particles or the masks that can partially block such particles eventually fail due to overloading. Ideally, these air conditioners can be upgraded to protect against the COVID-19 virus and others. However, this is a time consuming process and involves a lot of expenditure.

Therefore, there is an ongoing need to provide better systems and devices that are specifically designed to protect an individual from the COVID-19 virus and other microorganisms. If this can be done by destroying such harmful agents outside the human body, the fight against them in the body with resulting short term and long term complications can be avoided. The importance of such a reliable personal protection device cannot be overstated.

SUMMARY

The present disclosure relates to a portable system and apparatus for personal bio-protection that overcome the limitations of existing methods to prevent the exposure of individuals to disease causing microorganisms and other harmful agents. It also includes an endotracheal tube in fluidic communication with a ventilator. Present day conventional ventilators have no reliable way of destroying COVID-19 or other similar organisms. A way of destroying the viruses going into the ventilator is urgently needed. An air purification and disinfection system and methods of its use are urgently needed and are disclosed. The system includes an apparatus having a housing, ultraviolet disinfection chambers, an air mover, and an air-tight air distribution unit in communication with the housing that contains multiple disinfection chambers. Air is passed through the disinfection chamber where it is purified and disinfected before it is delivered to the user of the apparatus through the air distribution unit in the form of an air tight face mask which takes air exclusively coming from the unit, thus functioning as a "mask ventilator" or alternately through an endotracheal tube in fluidic communication with a ventilator. The apparatus can be configured as an open or a closed circuit system based on whether the exhaled air is released outside or sent back to the unit. In either case the inhaled air is exclusively from the unit and the individual takes no air from the outside. The system may be configured to purify air for an individual user in an airplane, a conference room, or a classroom as individually installed units, or as a totally portable unit for an individual user outside those facilities. As a portable unit the disinfection chamber can be incorporated into a back pack, a vest, a purse, a briefcase, a shoulder bag, a cervical collar, or any other format for being carried by the use outside those facilities.

The air purification and disinfection system for an individual can be coupled to a face mask or a ventilator. The system disinfects and purifies the air using UV (and in particular, Far-UVC and UV-C) radiation, HEPA filtration, carbon dioxide absorption, activated charcoal absorption, or any combination thereof. While the systems and apparatuses of the present invention are configured for disinfection and purification of air, it is also noted that as used herein, the term "disinfects" also implies both disinfection and purification.

According to an embodiment, an apparatus (or "device") can include: (a) a housing 110 having a housing inlet and a housing exit, wherein the housing is opaque to UV-C light; (b) an inner box 600 with multiple disinfection chambers embedded within the inner box, each chamber containing a number of UV-C light sources 602 arranged in a convoluted pattern, wherein each of the chambers have an air inlet and an air outlet; (c) an air mover; and (d) an air distribution unit in communication with the air outlet of the outer housing wherein the air distribution unit delivers purified and disinfected air to a user of the apparatus. The disinfection chambers use UV radiation that is strong, has close proximity to the microorganisms in the air and ensures the required duration of contact with the microorganisms by manipulating the speed of air movement by the air mover with multiple air flow settings.

According to an embodiment, an air purification and disinfection system comprises: (a) a housing having a housing inlet and a housing exit, wherein the housing is opaque to UV-C light; (b) an air mover in communication with the housing outlet or inlet, wherein the air mover controls a rate of air flow through the system; (c) an inner box with multiple disinfection chambers embedded within the housing and may be transparent to UV-C light, each chamber containing a number of UV-C light sources arranged in a convoluted pattern, wherein each of the chambers has an air inlet and an air outlet; and (d) an air distribution unit in fluidic communication with the air outlet of the outer box wherein the air distribution unit delivers purified and disinfected air to a user of the system.

According to an embodiment, an air purification and disinfection apparatus comprises: (a) a housing having a housing inlet and a housing exit; (b) a filter for removing allergens and microorganisms; (c) a pump; and (d) an air distribution unit in communication with the air outlet of the housing of the apparatus, wherein the air distribution unit delivers purified and disinfected air to a user of the apparatus.

According to an embodiment, a method of purifying and disinfecting an air flow comprises: (a) providing an apparatus having: (i) a housing with a housing inlet and a housing exit/outlet, (ii) an inner box with multiple disinfection chambers with an air inlet, an air outlet, and each disinfection chamber containing a number of UV-C light sources arranged in a convoluted pattern, (iii) an air mover, and (iv) an air distribution unit in fluidic communication with the air outlet of the housing of the apparatus; (b) an air mover controlling a rate of flow of an air source that moves through the apparatus; (c) moving the air source through the housing and into the disinfection chambers; (d) exposing the air source in close proximity to the UV-C light sources for a sufficient time period to disinfect the air source; (e) sending the disinfected air source to the air distribution unit; and (f) delivering the purified and disinfected air source to a user of the apparatus.

Various objects, features, aspects and advantages of the inventive subject matter will become more apparent from the following detailed description of preferred embodiments, along with the accompanying drawing figures in which like numerals represent like components

BRIEF DESCRIPTION OF THE DRAWINGS

FIG. 1B illustrates an exemplary portable air purification and disinfection system.

FIG. 2A is a schematic representation of an air disinfection chamber.

FIGS. 4A-4K illustrate several embodiments of a ventilator and methods of using the air purification and disinfection system in conjunction with a ventilator.

FIGS. 5A-5C illustrate one embodiment of a full face mask.

FIGS. 6A-6M illustrate different views of inner chamber of the air purification and disinfection system and internal details.

DETAILED DESCRIPTION

Figure 1A:
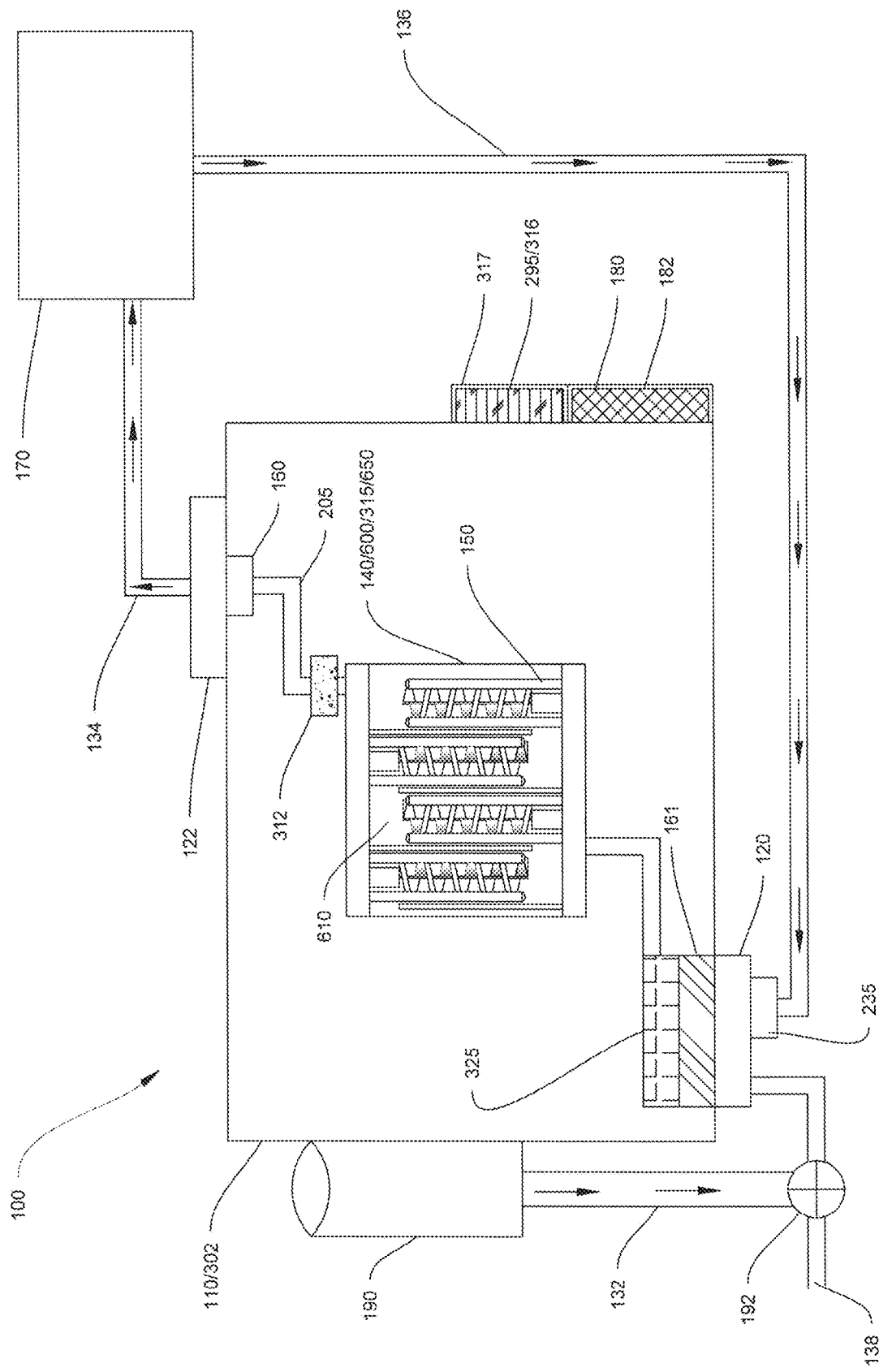
FIG. 1A is a schematic representation of an air purification and disinfection apparatus.

Characteristics and advantages of the present disclosure and additional features and benefits will be readily apparent to those skilled in the art upon consideration of the following detailed description of exemplary embodiments. It should be understood that the description herein, being of example embodiments, is not intended to limit the claims of this patent (or any patent claiming priority hereto). On the contrary, the intention is to cover all modifications, equivalents and alternatives falling within the spirit and scope of this disclosure and the appended claims. Many changes may be made to the particular embodiments and details disclosed herein without departing from such spirit and scope.

As used herein and throughout various portions (and headings) of this patent (including the claims), the terms "invention", "present invention" and variations thereof are not intended to mean every possible embodiment encompassed by this disclosure or any particular claim(s). Thus, the subject matter of each such reference should not be considered as necessary for, or part of, every embodiment hereof, or of any particular claim(s), merely because of such reference. Each of the appended claims defines a separate invention, which for infringement purposes is recognized as including equivalents to the various elements or limitations specified in the claims. Depending on the context, all references below to the "invention" may in some cases refer to certain specific embodiments only. In other cases, it will be recognized that references to the "invention" will refer to subject matter recited in one or more, but not necessarily all, of the claims. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (for instance, "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms are used herein. To the extent a term used in a claim is not defined, it should be given the broadest definition persons in the pertinent art have given that term as reflected in printed publications and issued patents at the time of filing.

The present disclosure relates to a system and apparatus for personal bio-protection that overcomes the limitations of existing systems to prevent the exposure of individuals to disease causing microorganisms and other harmful agents and more importantly to prevent the harmful agents and microorganisms getting the into human body. The purpose is to destroy such organisms and agents outside the human body. An air purification and disinfection system and methods of its use are disclosed. The system includes an apparatus having a housing, an inner box with multiple ultraviolet disinfection chambers, an air mover, and an air distribution unit in fluidic communication with the housing. Air is passed through the disinfection chambers where it is purified and disinfected before it is delivered to the user of the apparatus through the air distribution unit. The apparatus can be configured as an open or a closed circuit system. The personal system may be configured to purify air for an individual in an airplane, a conference room or a classroom, or as a portable unit for an individual user anywhere else. As a portable unit the disinfection chamber can be incorporated into a back pack, a vest, a purse, a briefcase, a shoulder bag, a cervical collar, or any other format for being carried by the user.

The present invention relates to an air purification and disinfection apparatus, and in particular, to a device that eliminates harmful airborne particles and microorganisms from ambient air as it passes through the device before the purified air is delivered to an individual who will be inhaling air exclusively from the unit. Alternately the air circulator 160 (pumps) can be installed at the base of the housing outlet/exit 122. One embodiment of the air purification and disinfection apparatus 100 is shown in FIG. 1. The air purification and disinfection system or apparatus 100 includes a housing 110 having an inlet 120 and an outlet/exit 122, wherein the housing is opaque to UV-C light; a transparent/opaque inner box 140 with multiple ultraviolet disinfection chambers 610 embedded within the housing, wherein the chambers contain a plurality of UV-C emitting light sources 150; a purified air distribution unit 170 in fluidic communication with the housing outlet/exit 122 and the air disinfection unit 140, also called a disinfection box; a power source 180 with a battery 182; a Printable Circuit Board (PCB) 295/316 enclosed in a PCB enclosure 317; and an air circulator 160. The air purification and disinfection apparatus 100 may be configured to have fewer or more components than shown in FIG. 1A.

A perspective view of one embodiment of the system 100 is seen in FIG. 1B. This embodiment shows a half face mask 508 as the purified air distribution unit 170, the housing 110 as an opaque back pack, the housing air intake 120 receiving air flow from the canister 190 and the user's exhaled air from the face mask 508 through tube 136. The apparatus 100 is designed to provide a continuous source of purified and/or disinfected air for an individual user (e.g., a healthcare worker, a first responder, or a staff member at an assisted care facility) and to provide a practical solution that can prevent exposure of individuals to infection and contaminants by isolating/protecting the person substantially from the surrounding contaminated and/or impure air and allowing the individual to breath in air exclusively from the unit where the organisms are destroyed thus making sure that the organisms are destroyed outside the human body.

Housing

The housing 110 for the air purification and disinfection apparatus 100 substantially contains or is connected to all the components of the air purification and disinfection apparatus. The walls of the housing 110 are typically made of a material that is opaque to UV-C light thereby blocking the leakage of UV-C and far UV-C light so that there is no UV-C harm done to the person using the device or people around the user.

The housing has an inlet 120 that allows for the entry of ambient air or another approved source of air. In an open circuit embodiment, all or the majority of the air entering the inlet 120 of the housing is ambient air; however, another air stream, such as an oxygen enriched air stream, may also be permitted to enter the device 100 for purification or decontamination. Alternative closed circuit embodiments recycle, purify and disinfect the air inhaled and exhaled from the user of the device in addition to the ambient air and the supplemental oxygen.

The housing also has an outlet/exit 122 that allows for the exit of the purified or decontaminated air from the housing. The air exiting the housing through outlet/exit 122 is generally delivered to a purified air distribution unit 170, such as a mask or a ventilator through tube 134

The air purification and disinfection apparatus 100 may utilize an air mover 160 or 161 circulator (such as an air pump 160/161 or a fan 203) in communication with the inlet 120 to ensure a controlled rate of air flow through the device 100 by selecting one or other of multiple power settings in 160/161.

Figure 3A:
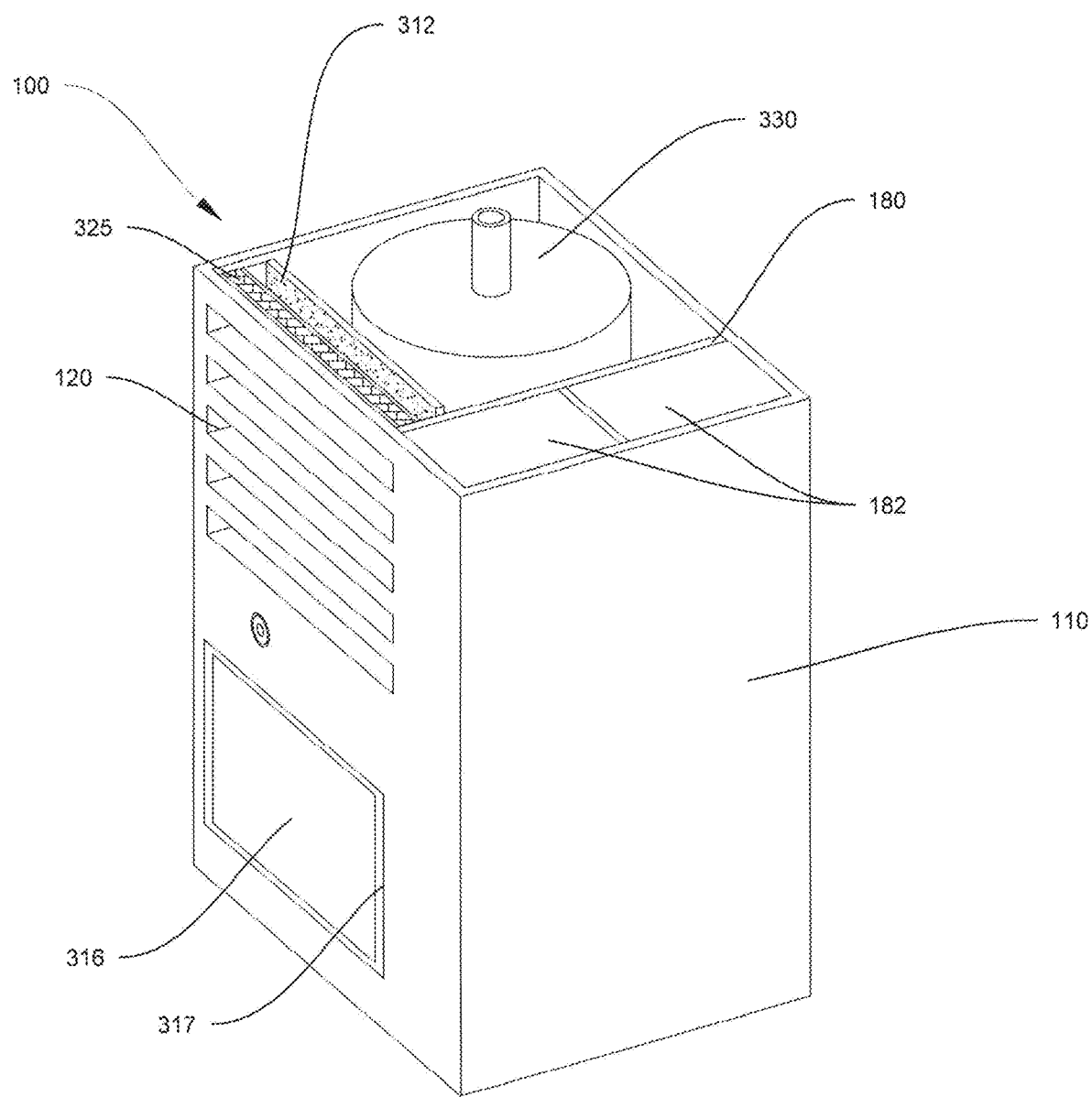
FIG. 3A is a perspective view of another embodiment of the air purification and disinfection apparatus with its top removed.

The housing 110 can take on any configuration (e.g., a backpack, a box, a briefcase, a shoulder bag, a briefcase, or a cervical collar). One embodiment of the apparatus housing 110 and its contents is shown in FIG. 3A. FIG. 3A shows an air purification and disinfection apparatus 100 without a UV-C disinfectant chamber. The apparatus shown includes a pump 330, batteries 182, an activated carbon filter 312, a HEPA filter 325, and a Printable Circuit Board (PCB) 295/316 enclosed in a PCB enclosure 317. The pump 330 draws in a mixture of external/ambient air and exhaled air through the inlet 120 with or without supplemental oxygen. The air source entering the inlet 120 may be oxygen enriched. Once it enters the inlet 120 the air is filtered first through a HEPA filter 325 and then through an activated carbon filter 312. The filtered and purified air flow is then pumped out to an air distribution unit 170. Batteries 182 are provided for powering the pump 330 and the PCB. The PCB can be configured to enable control of the air flow and other functions of the apparatus. This embodiment is particularly useful to protect a user from allergens or harmful vapors.

Figure 3B:
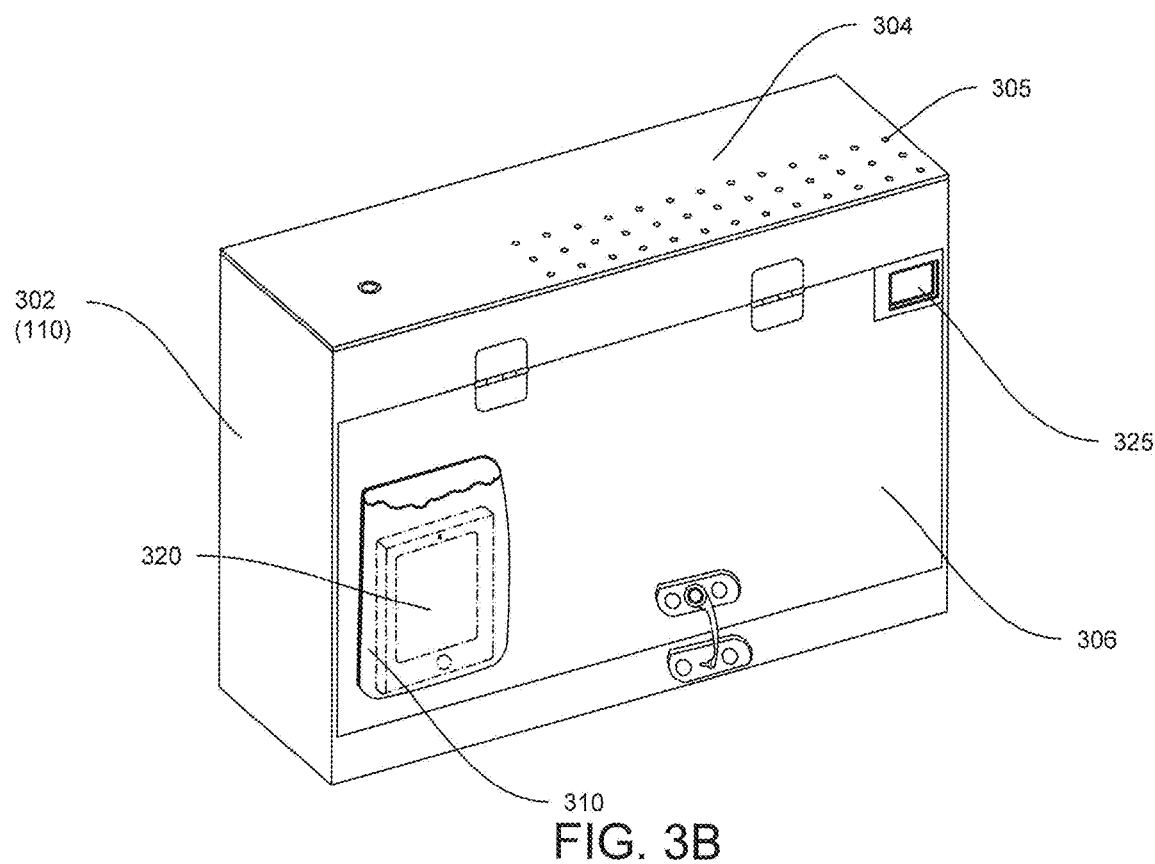
FIGS. 3B-3C illustrate an embodiment of the air purification and disinfection system housing.
Figure 3C:
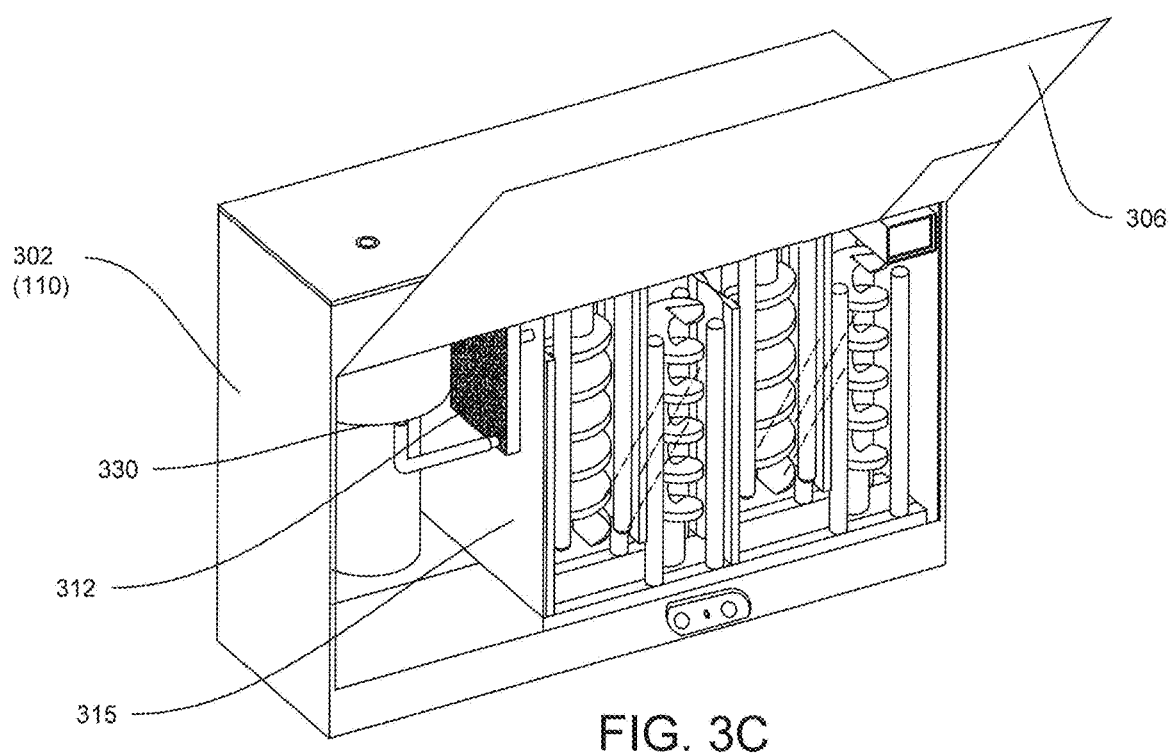

FIGS. 3B-3C illustrate yet another embodiment of the housing 110. The housing in this example is an outer box 302 having a top cover 304 with a plurality of holes 305 for dissipation of heat from inside the housing, a back cover 306, a HEPA filter 325, a pocket 310 for holding a phone or a PC 320, and an inner box 315 or disinfection chamber 140 located inside the outer box 302, as shown in FIG. 3C. The inner box 315 is configured to house a plurality of UV-C disinfection chambers 610 (as disclosed, for instance, in FIGS. 6C and 6D) through which the air can flow in a combination of serpentine as well as helical paths.

Air Purifiers/Enhancers

Filters. As shown in FIG. 1A one or more filters may be used to decontaminate the air supplied to the user of the apparatus 100. A filter 325 may be positioned at a base of the housing 110 to filter the incoming airflow. For example, airflow entering the inlet 120 may be filtered to filter out fine particulates and/or microorganisms. Exemplary filters are High Efficiency Particulate Air filters (i.e., HEPA filters) or 0.22 micron filters. Alternatively, an inline replaceable carbon dioxide absorbent filter 235 may be used on the line bringing air into the housing 110 from the air distribution unit 170. In some embodiments, an activated carbon filter 312 can be used after the UV-C disinfection chamber to filter the purified air before it is sent to the distribution unit 170.

Oxygen Source or Concentrator. The air purification and disinfection apparatus 100 can also include an air/oxygen source, such as, a canister of oxygen or an oxygen concentrator, in fluidic communication with the device 100. For example, a canister 190 can be selectably attached to the housing 110, either attached to the outside of the housing or within the housing. One embodiment of an oxygen canister 190, illustrated in FIG. 1, is attached to the outside of the housing. In this embodiment a first end of the tubing 132 is connected to the canister, while a second end of the tube 132 can be directly connected to inlet 120 of the device or the oxygen can be mixed with ambient air before entering the inlet 120 by connecting the second end of tube 132 to an air control mixing valve 192. The ambient air will be supplied to valve 192 through an air inlet 138. The ratio of oxygen to air may be electronically controlled through the mixing valve 192.

Figure 2B:
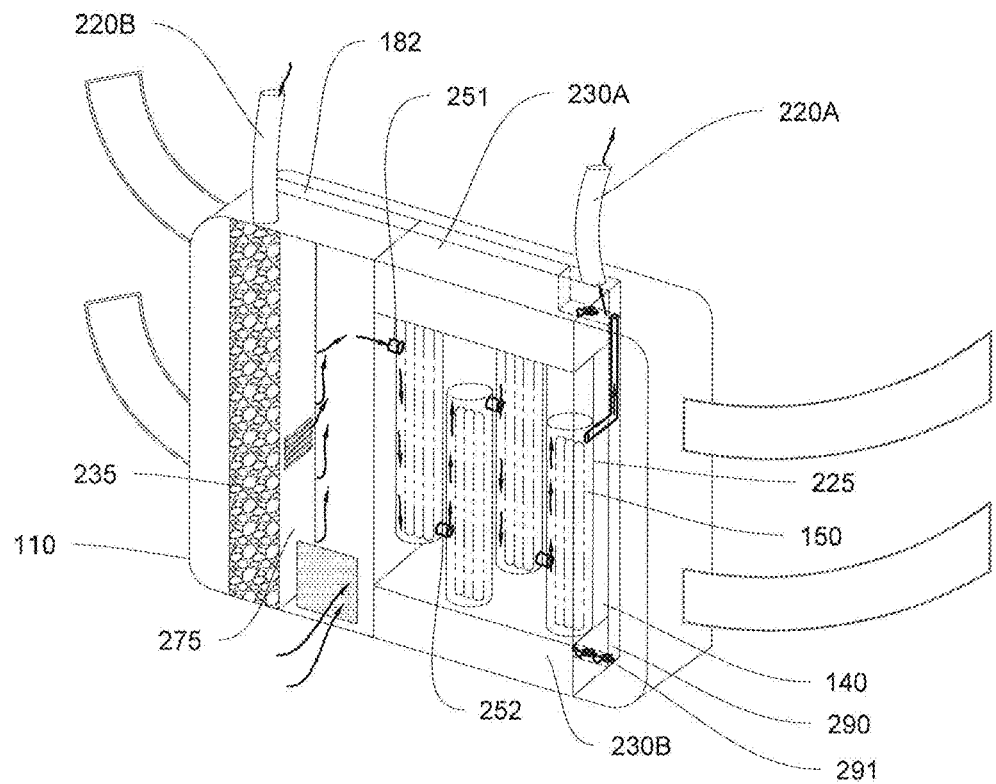
FIGS. 2B-2D illustrate examples of a housing and disinfection chamber of an air purification and disinfection system.
Figure 2C:
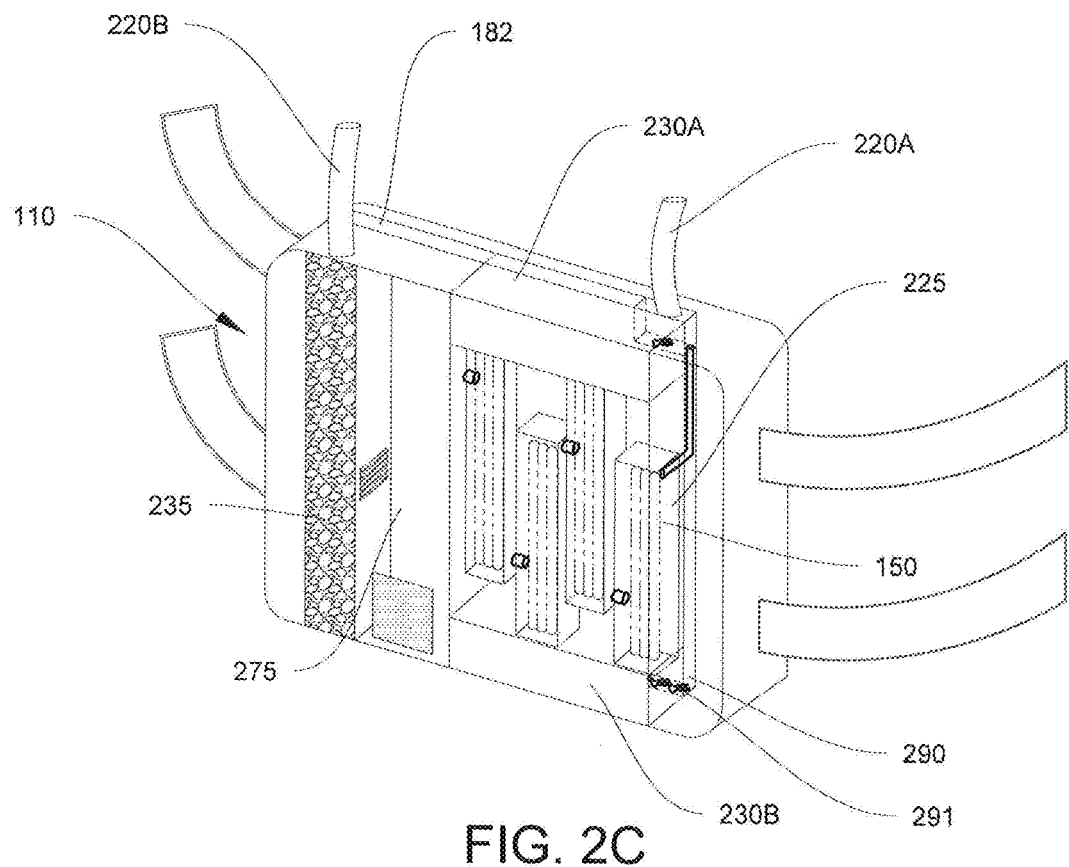
Figure 2D:
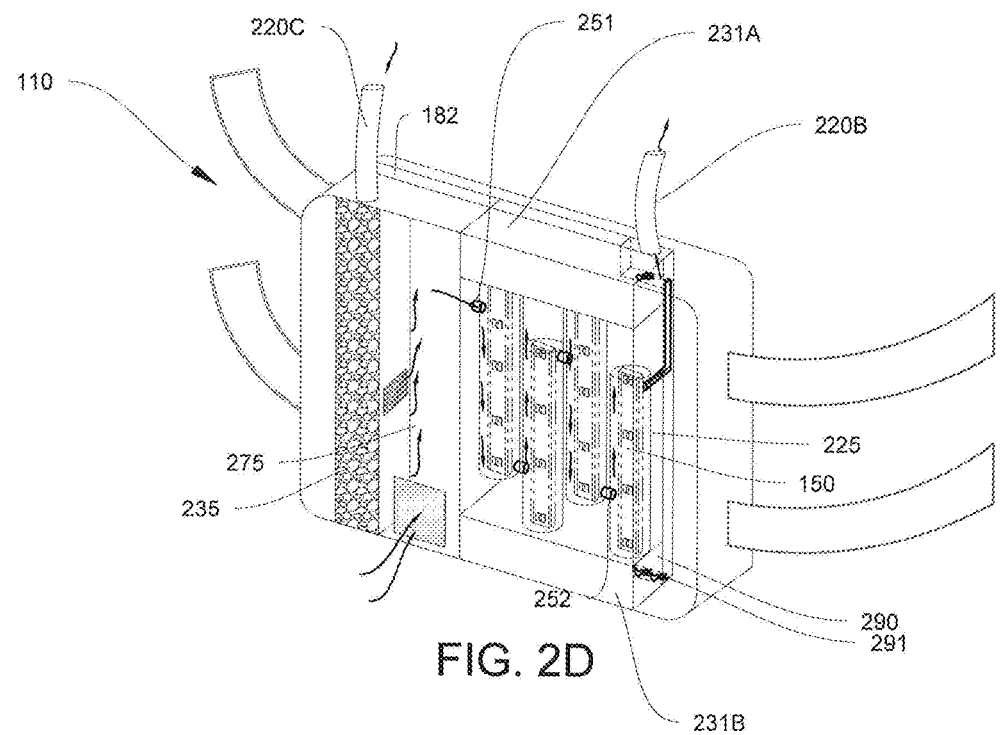

Similarly, an oxygen concentrator 275 as depicted in FIGS. 2B, 2C & 2D can be used to treat air and concentrate oxygen to a desired level for the user. Patients with chronic obstructive pulmonary disease or other respiratory ailments can utilize this feature to process their oxygen supply. The oxygen concentrator 275 is often placed inside of the housing 110 as shown in FIG. 2B.

Carbon Dioxide Absorption Unit. A carbon dioxide absorption unit 235 may also be included in the air purification and disinfection apparatus 100. As illustrated in FIG. 2B, the carbon dioxide absorption unit may be positioned in the housing 110. One embodiment of the carbon dioxide absorption unit 235 is a replaceable canister having a material that can absorb carbon dioxide from an incoming airflow. The material can include, without limitation, soda lime, Baralyme™, or Amsorb®. The air passing through a carbon dioxide absorption unit 235 will be substantially free of carbon dioxide and may be sent to the oxygen concentrator 275 to be further processed. In an otherwise healthy individual where there is no virus load in the exhaled air, the exhaled air can be released out of the mask and there is no need for the carbon dioxide absorption canister.

Activated Charcoal Filter Unit. An activated charcoal 312 placed between the inner box (140,600,315) and the pump (160, 330) can filter out any heavy metal or other fumes that might escape from the inner box (140,600,315) with its disinfection chambers 610, 622, 225. By placing an activated carbon absorption unit in an air pathway of the air purification and disinfection apparatus 100, heavy metal fumes, volatile organic compounds, or other toxic/poisonous vapors can be absorbed and removed.

Disinfection Chamber

The housing 110 has an inner box 140 enclosing multiple disinfection chambers 610 embedded within the housing. The walls of the inner box 140 are typically made of a material that is either transparent to UV-C light or opaque to UV-C light. The disinfection chambers 610 have a number of UV-C light sources 150 mounted within the chambers 610. The inner box 140 will have an air flow inlet 210 and an air flow outlet 205 as shown in FIG. 2A. FIG. 2A represents only the inner box 140 of the housing 110 of unit 100.

Pump/Fan/Air Mover

This can be in the form of a pump (314, 330, 161) or a series of fans 203 as in FIG. 2A. In one embodiment the pump 160 (from FIG. 1A), 330 (from FIG. 3C), 314 (from FIG. 6E) is placed just before the outlet of housing 110. The pump moves air through the entire system: (a) the housing, including all filters and the inner box 140 (from FIG. 1A), 600 (from FIGS. 6A, 6B), 315 (from FIG. 3C) with its disinfection chambers, and (b) into the air distribution unit 170 (from FIG. 1A). The pump functions at different power levels that can be electronically controlled. By altering the power level of the pump, the air circulation can be made faster or slower. The pump pressure levels also determine the air pressure inside the sealed airtight distribution unit 170. In the case of 170 this will be adjusted to the comfort level of the individual breathing through the mask.

UV Light Sources

UV light is a well-known disinfectant/decontaminant. Many UV light emitting devices are available in the marketplace. These devices are used to "sterilize" surgical suites, airports, and other such spaces. However, for effective disinfection/decontamination, the UV light has to be strong enough to destroy/kill the microorganisms from close, direct proximity. Additionally, the microorganisms have to be exposed to the UV light for a sufficient duration of time before they can be neutralized. Such high energy UV radiation and long exposure to UV radiation can injure normal human cells like skin, cornea, and other cells. Therefore, UV light should not be allowed to come near the hands or other area of the skin. Furthermore, exposure of skin to UV radiation can cause skin irritation and other ailments.

There are UV protected free standing air filtration and disinfection systems available in the market. These units are installed inside the rooms where people can move around freely without risk of UV-C radiation. Such units treat only portions of the room air and so the rest of the room will still contain a virus load. This is similar to using a fan with a sealed back to flush away smoke. There is a smoke free area just in front of the fan but not in the rest of the room. Similarly, the currently available UV-C free standing disinfection units inside a room will clear the virus from an area in front of the unit, while leaving the rest of the room with the same virus load. Even though the continuous working of these units can reduce the virus load, if there is no additional virus loads coming into the room.

UV light is electromagnetic radiation beyond the wavelength of the visible violet or beyond the spectrum that the human eyes can see. The UV light itself has a spectrum ranging from a 100 nanometer to 400 nanometers. UV of wavelengths from 315 nm to 400 nm is called UV-A, from 280 nm to 315 nm UV-B, and from 200 nm to 280 nm UV-C. Far UV-C light has a spectrum ranging from 207 nm-222 nm. For the purposes of this application, the terms "UV-C/UVC/far UV-C/far UVC" are used interchangeably herein.

The earth's ozone layer blocks the UV-C, but allows UV-A and UV-B to reach earth. The shorter the light wavelength is, the less it will penetrate human skin. UV-A and UV-B can damage human skin and are the ones implicated in sunburn, skin cancer, and an increased risk of cataracts. UV-C from the sunlight cannot normally reach the earth because it is filtered out by the earth's ozone layer. Far UV-C and UV-C light penetration into the skin is low, but is sufficient to cause some damage. However, UV-C light does penetrate microorganisms and denature the RNA/DNA of those microorganisms, causing cell damage and making the reproduction of those microorganisms impossible.

The kill rate of UV-C light depends on the specific microorganism you are trying to destroy as well as the UV-C dosage the organism receives. Dosage (J/m2) is a combination of exposure time and intensity (microwatts per square centimeter). UV_dose=UV_bulb_power*Exposure_time/(4*pi*UV_bulb_distance^2. The intensity is a measure of the power of the UV-C and its proximity to the organism, where Intensity, E=UV_bulb_power/UV_bulb_distance^2.

The number, type, and the placement of the UV-C bulbs 150 in the disinfection chambers will ensure that the bacteria and viruses in the air flow passing through the disinfection chambers 610 will receive a sufficient UV-C dosage to kill any microorganisms in the air.

The UV-C light sources 150 can be any type of UV-C light source. UV-C light sources may include mercury lamps, fluorescent tubes, pulsed xenon lamps, excimer lamps, UV-C LEDs, and UV-C lasers. Once the UV-C bulb is selected and the wattage or irradiance is known, the exposure time to achieve the desired dosage can be calculated and the appropriate time for the air path to spend passing through the disinfection chambers in close proximity to the UV-C lights can be determined. The speed of air movement is adjusted to meet this demand by adjusting the power levels in the air mover 160/161 (from 1A), 330 (from 3C), and 314 (from 6E). A convoluted air path through the disinfection chambers will extend the time that the air spends passing through the chambers 610. The time the air spends in the disinfection chambers is further controlled by the speed of air movement through the chambers as controlled by the air mover.

One exemplary embodiment of the disinfection box 140 is illustrated in FIG. 2A. The entire FIG. 2A represents only the inner box 140 of housing 110 of unit 100. Here the inner box 140 has to be opaque because there is no outer box 110. Optionally, one or more miniature fans 203 are positioned at the base of an inner box 140. The fans 203 are configured to draw air through the disinfection air inlets 210 into the disinfection box 140. The disinfection box includes multiple air disinfection chambers separated by sheets 207. Each sheet 207 includes a plurality of UV light sources 150 which are configured to emit far UV-C light. The UV light sources 150 can be cylindrical UV-C lamps or UV-C LEDs. As shown in FIG. 2A, for example, the sheets 207 can be arranged in such a manner that a serpentine airflow pathway is created through the disinfection chambers 610 for the incoming airflow inside the disinfection box 140. For instance, a gap is created between two adjacent sheets 207 such that the airflow can pass around the sheets in a serpentine manner providing an air flow path that is in close proximity to the UV-C lights 150. Increasing the number of sheets 207 and the twists and turns in the serpentine path will increase the time that the airflow will spend inside the chamber 140.

Other exemplary embodiments of the disinfection box 140 are shown in FIGS. 2B-2G, 650 as shown in 4B-4K and 600 as shown in 6A-6H. The disinfection box includes multiple UV-C light sources 150 enclosed within cylindrical or rectangular containers/chambers 225 which behave like disinfection chambers 610. Each cylindrical or rectangular container/chamber housing the UV-C light sources has an airflow inlet 251 and an airflow outlet 252 that are commonly on opposed ends of the container. As shown in FIG. 2B, an airflow outlet from a first cylindrical container/chamber may be in fluidic communication with an airflow inlet of a second cylindrical container/chamber and so on. Thus, the disinfected outflow from the first cylindrical container/chamber can enter the second cylindrical container/chamber where it is again exposed to UV-C light. The disinfected outflow from the second cylindrical container/chamber can then enter a third cylindrical container/chamber where it is again subjected to further disinfection. The container/chamber are optionally lined with reflective material and titanium dioxide to concentrate the UV-C and also to make the device more lethal to the microorganisms in the air flow. The reflective and titanium dioxide coatings can be one over the other or can be in alternate up and down full length longitudinal strips inside the containers/chambers, and all other relevant surfaces.

Figure 2E:
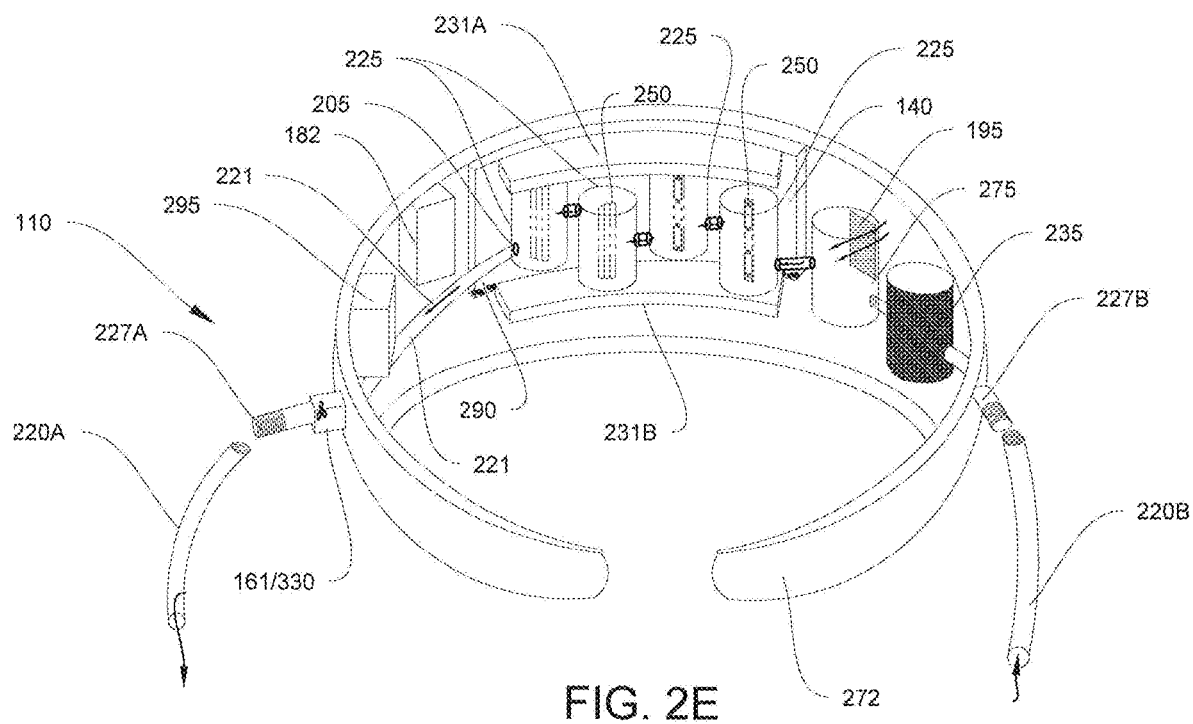
FIGS. 2E-2G illustrate an exemplary embodiment where the housing is configured as a cervical collar.

The cylindrical or rectangular containers/chambers 225 are attached to upper ballasts 230A and lower ballasts 230B. An optional cooling chamber 290, equipped with one or more small fans 291, in communication with the disinfection box 140 may be positioned to dissipate any heat generated by the large number of light sources operating within close proximity to each other within the disinfection box 140. FIGS. 2D and 2E illustrate other embodiments of the UV-C light sources. In these embodiments, the disinfection box 140 includes UV-C LED light sources 150 enclosed in containers/chambers 225 attached to upper and lower LED drivers 231A and 231B respectively.

Each cylindrical or rectangular enclosure/chamber housing the UV-C or UV-C LED light sources has an airflow inlet 251 and an airflow outlet 252 that are commonly on opposed ends of the enclosure or container. As shown in FIGS. 2D and 2E, an airflow outlet from a first cylindrical container/chamber may be in fluidic communication with an airflow inlet of a second cylindrical container/chamber and so on. Thus, the disinfected outflow from the first cylindrical container/chamber can enter the second cylindrical container/chamber where it is again exposed to UV-C light. The disinfected outflow from the second cylindrical container/chamber can then enter a third cylindrical containers/chambers where it is again subjected to further disinfection. The containers/chambers are optionally lined with reflective material and titanium dioxide to concentrate the UV-C and also to make the device more lethal to the microorganisms in the air flow. The reflective and titanium dioxide coating can be one over the other or can be in alternate up and down full length longitudinal strips on the inside of the cylindrical/rectangular containers/chambers.

The ballasts and/or LED drivers that run the UV-C light sources 250 can be along the upper and lower borders of the disinfection box 140. The cylindrical or rectangular chambers or containers 225 can hang down from the top ballasts or drivers or project up from the bottom ballasts or LED drivers in an alternating fashion. For instance, a first and third container/chamber 225 can be connected to a top ballast/LED driver and a second and fourth container/chamber can be connected to a bottom ballast/LED driver. By alternately turning on and off the first and third and the second and fourth containers/chambers, heat production can be minimized and the life of the UV-C sources can be extended. Any additional cylinders and ballasts arrangement can be planned in a similar fashion.

The disinfection box 140 illustrated in FIGS. 2B-2E further include a carbon dioxide absorption unit 235, an oxygen concentrator 275, a battery 182 as the power source 180, a PCB (not shown), and a cooling chamber 290.

Figure 2F:
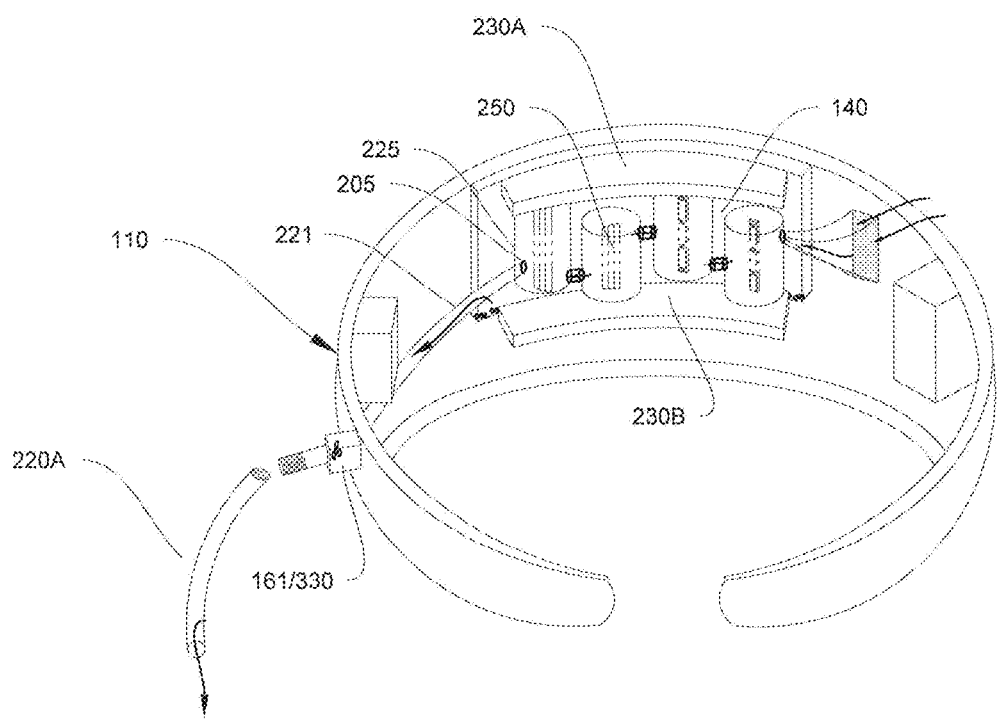
Figure 2G:
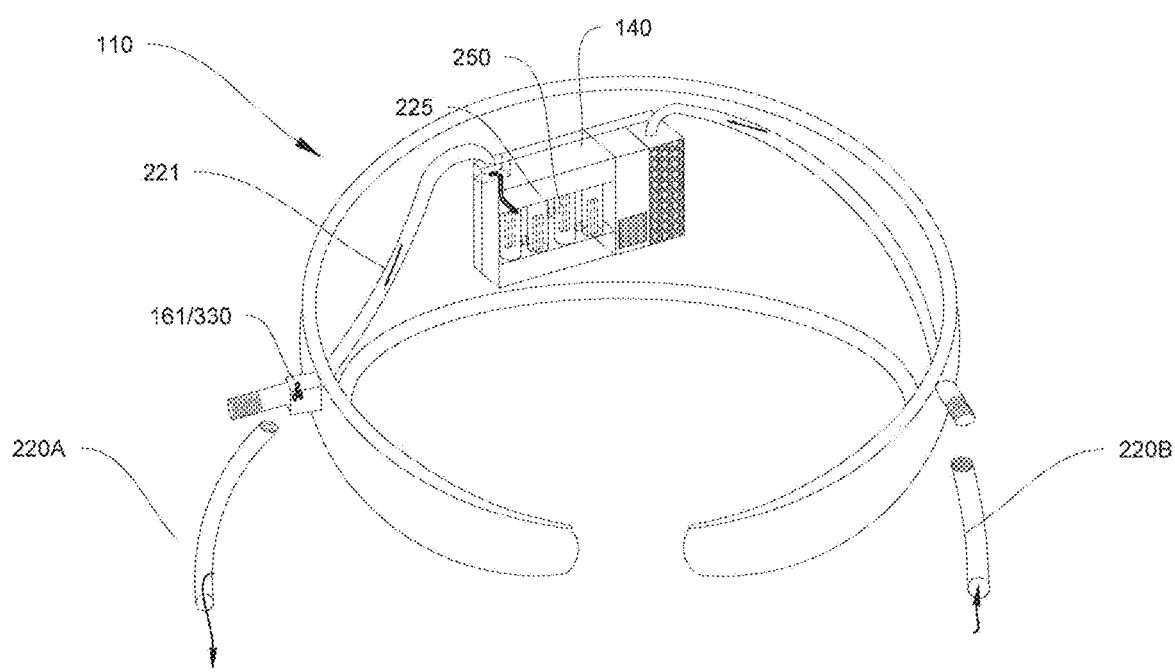

Other embodiments of the apparatus 100 configured as a cervical collar are shown in FIGS. 2F and 2G. FIG. 2F illustrates a cervical collar 110 that includes a UV-C disinfectant box 140. The disinfection box 140 includes a combination of one or more UV-C source tubes 150 enclosed in cylindrical chambers or containers 225 attached to upper ballast 230A and lower ballast 230B, while FIG. 2G shows one or more UV-C LED lights 150 that are enclosed in cylindrical chambers/containers 225 attached to upper LED drive 231A and lower LED drive 231B.

The light sources can generate heat so that a heat sink or other type of cooling unit 290 can be incorporated in close contact with the UV-C sources to carry the heat away from the circulating UV-C treated air. The extracted heat is then expelled through from the collar using small fans 291 at the bottom of the collar, behind the chambers/containers 225. The partitions and the chamber walls can be coated with either one or both a reflective material and titanium dioxide. The multiple reflections of the UV-C will impinge the microorganisms on all sides, and the titanium dioxide can augment the lethal property of the disinfection chamber towards all microorganisms. As shown in FIGS. 6I-6M, the surface of these reflecting and titanium dioxide coated walls can be made irregular to increase the light reflection and distribution to the passing air containing the microorganisms.

As illustrated in FIGS. 2B to 2G, the air purification and disinfection apparatus includes a disinfection box 140, a carbon dioxide absorption unit 235, oxygen concentrator 275, battery 182 with PCB provision, and cooling chamber 290. An air-filled cushion tube along the bottom and top of the collar on the inside (not shown) will prevent the collar from hitting the back of the user's neck uncomfortably.

Optionally a tube 221, as shown in FIGS. 2F to 2G can be built into the collar to provide purified, disinfected air from the UV-C disinfectant box outlet 205 to the bottom of the collar on a second side where the air goes out through a pump 161/330 and a threaded outlet or spout 227A. The tube 220A can be coupled to spout 227A to carry the air to the inlet of an air distribution unit 170.

FIG. 2G illustrates another embodiment of the housing 110 configured as a wearable cervical collar. As shown, the disinfection box is devoid of a carbon dioxide absorption unit and oxygen concentrator having only UV-C tubes 250 enclosed in cylindrical chambers or containers 225 and the HEPA filter.

FIGS. 6A-6D illustrate details of yet another embodiment of a disinfection box 140. FIGS. 6A-6D show the inner box 600 made of a transparent/opaque material, wherein a plurality of UV-C light sources 602, a plurality of ballasts 604, a plurality of dividers 606, and a plurality of helixes or helical airflow diverters 608 make up more than one disinfection chamber 610. Box 600 represents box 140 taken out of the outer box 110 in FIGS. 1A & 6E. This is only to highlight the details of the inner box 140 containing multiple disinfection chambers 610.

Figure 6A:
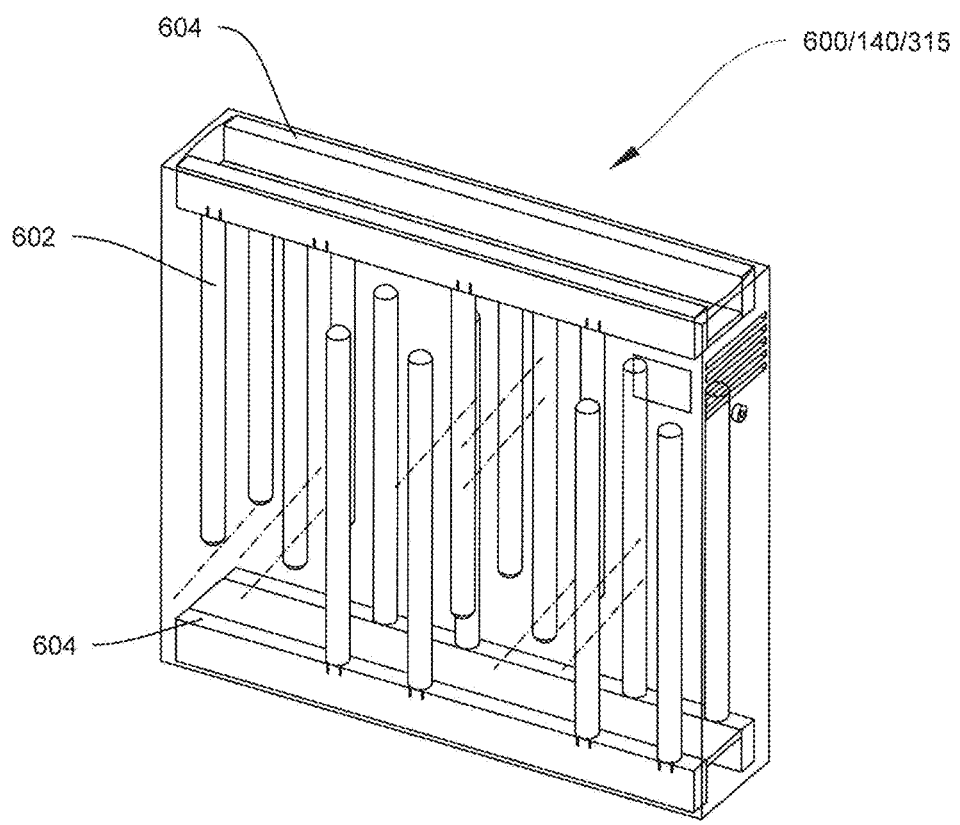

FIG. 6A shows internal details of the inner box 600 without the dividers 606 and the helixes 608 to highlight the arrangement of the ballasts 604 and the UV-C tubes 602. The ballasts 604 can be positioned along the upper and lower sides of the inner box 600 and groups of the UV-C tubes 602 can hang down from the upper ballasts 604 or project up from the bottom ballasts 604 in an alternating fashion. The exemplary illustrations of FIGS. 6A and 6C show four groups of four UV-C tubes 602 in each disinfectant chamber 610, however any other number is well within the scope of the present disclosure.

Figure 6B:
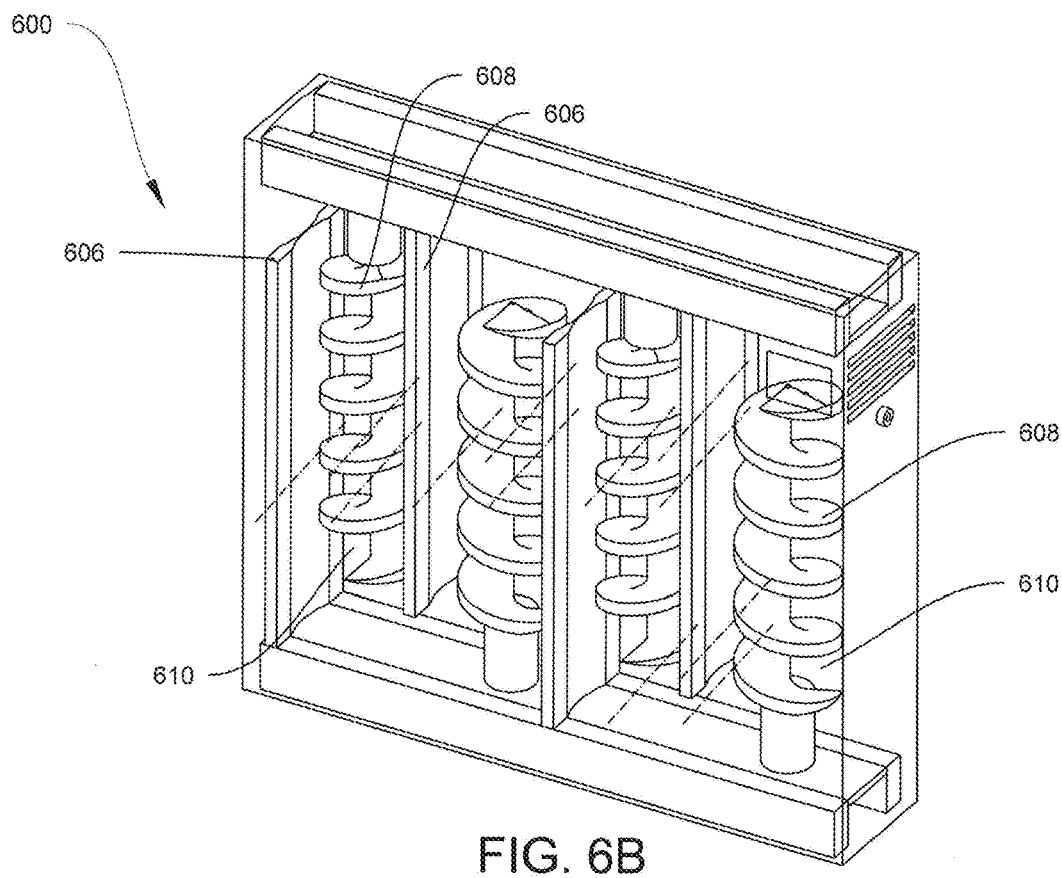

FIG. 6B shows the internal details of the inner box 600 without the UV-C tubes 602 to highlight the arrangement of the dividers 606 and the helixes 608. As can be seen, the dividers 606 are arranged in parallel and divide the inner box along a length of the inner box 600 to form the plurality of disinfectant chambers 610 oriented along a width of the inner box 600. The dividers 606 are attached to the sides of the inner box in an air tight fashion and are arranged in a staggered manner with the alternate dividers 606 providing a passage for the air between the adjacent disinfectant chambers 610 on the top and bottom ends. The passage provides the functionality of the inlet and the outlet for the adjacent disinfectant chambers 610 and enabling flow of the stream of air through the plurality of disinfectant chambers 610 in a zig-zag manner along the length of the inner box 600. Each disinfectant chamber 610 includes a helical airflow diverter 608 configured to create a helical path for the stream of air along a length of the disinfectant chamber 610 and to expose microorganisms in the airflow to UV-C or far UV-C light emitted by the ultraviolet light sources for an extended and optimal duration, with close contact. The inside of each disinfection chamber 610 can be lined with layers of reflecting material and titanium dioxide that are applied one over the other or in alternating strips and can have a smooth or rough surface.

Figure 6C:
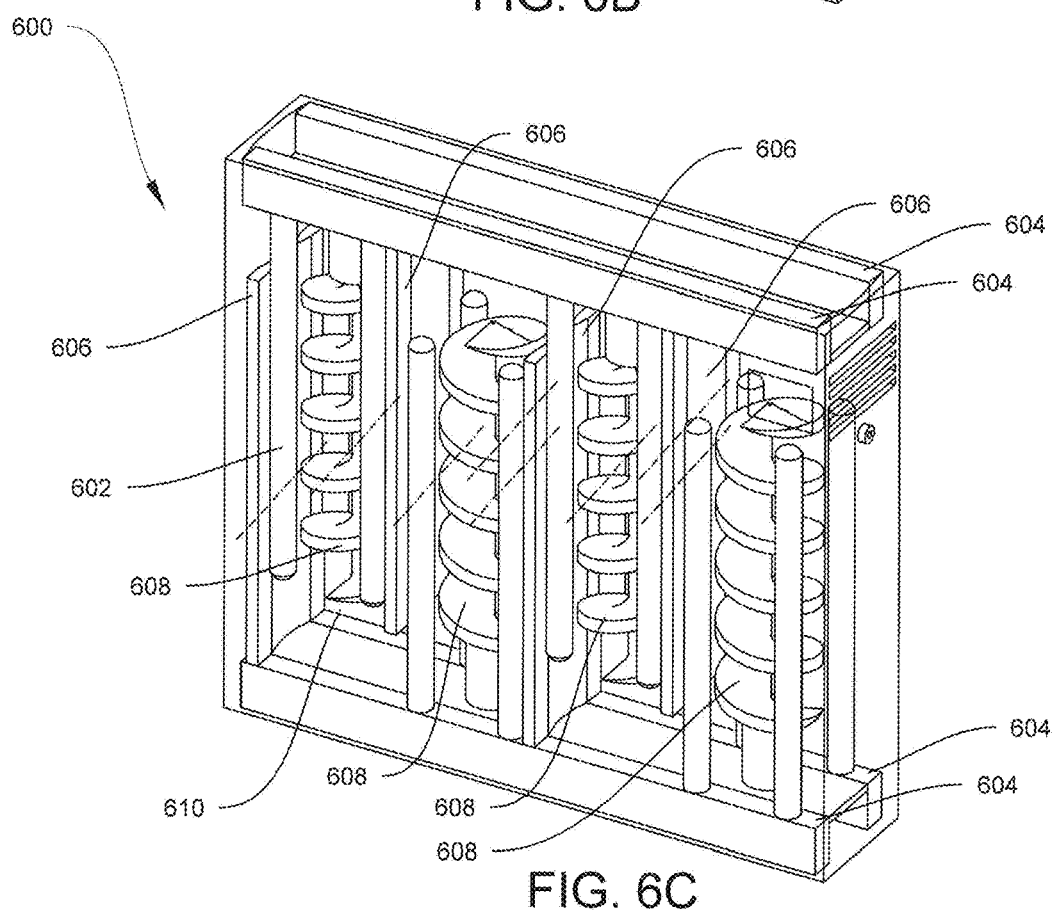

FIG. 6C shows all the internal parts of the inner box 600, i.e., the UV-C tubes 602, the dividers 606 and the helixes 608. As can be seen, the groups of the UV-C tubes 602 are located such that each group lies between two adjacent dividers 606 (thereby making up a disinfectant chamber 610), and the UV-C tubes 602 of the group in each disinfectant chamber 610 are located such that the corresponding helical airflow diverter 608 is covered front and back by the UV-C tubes 602 to irradiate the air flowing through the disinfectant chamber 610 in helical manner continuously, in close proximity and for a long and needed duration.

Figure 6D:
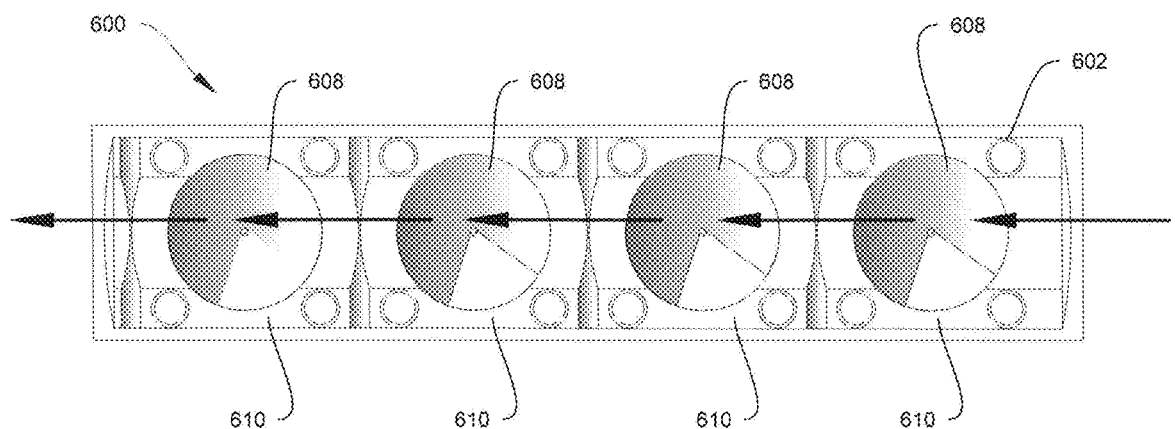

FIG. 6D shows a top view of the inner box 600 showing the sequential flow of air from right to left through different disinfectant chambers 610, wherein the flow in each individual chamber 610 is helical due to the presence of the helical airflow diverter 608, and zig-zag or serpentine as air moves from one disinfectant chamber 610 to other due to change in direction of the flow by 180 degrees on account of the configuration of the dividers 606 inside the disinfectant chambers 610, thereby providing an extended exposure to UV-C radiations.

Figure 6E:
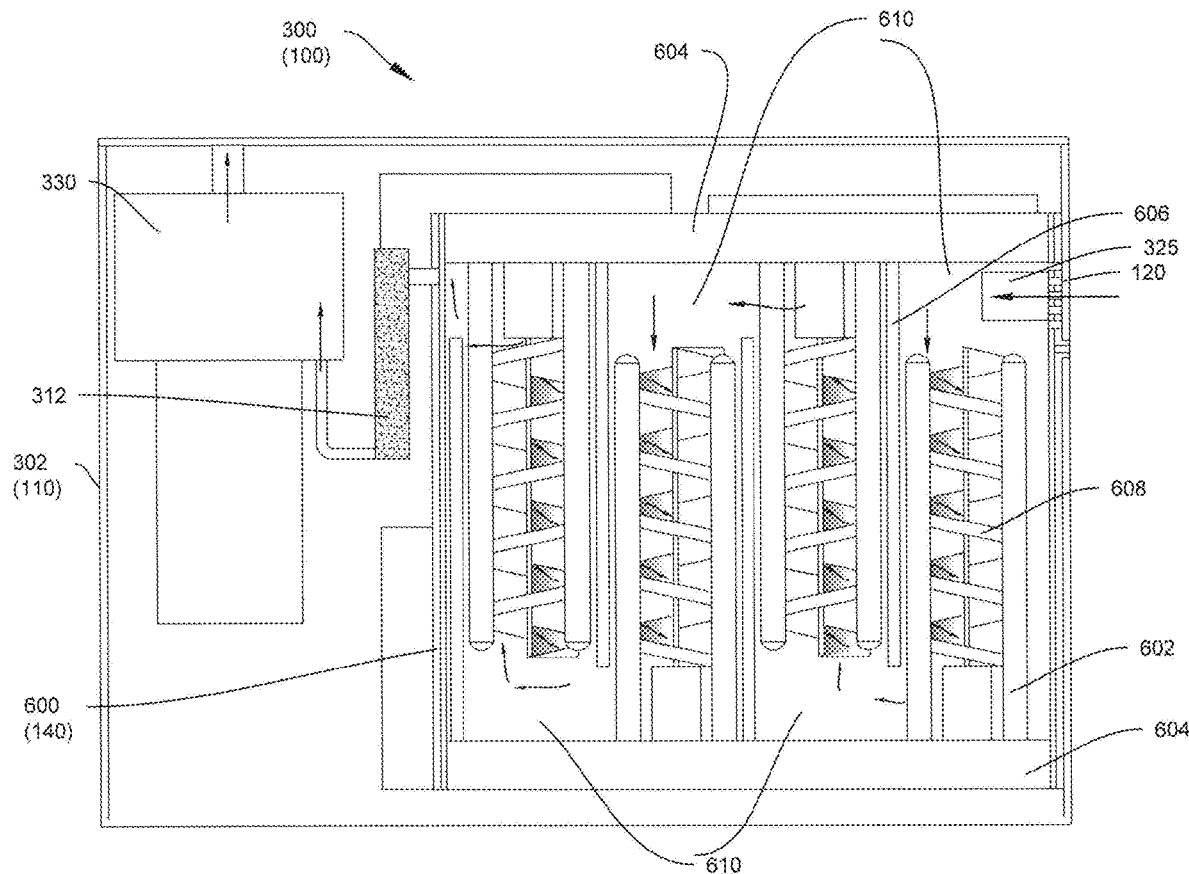

FIG. 6E illustrates unit 300, same as unit 100, how the inner box 600 is placed within the housing 110 or outer box 302/110. The pump 314/330 draws in ambient air through the inlet 120. Once the air enters the inlet, it is filtered through a HEPA filter 325 before entering the inner box 600/315/140. The inner box 600 is configured to house a plurality of UV-C disinfectant chambers 610 (as disclosed, in FIGS. 6B, 6C, and 6D) and 622 (as disclosed in FIGS. 6G and 6F) through which the air can flow in a combination of serpentine as well as helical paths. The disinfected air may then be filtered through an activated charcoal filter 312. The purified and disinfected air is then pumped out to an air distribution unit 170.

Figure 6F:
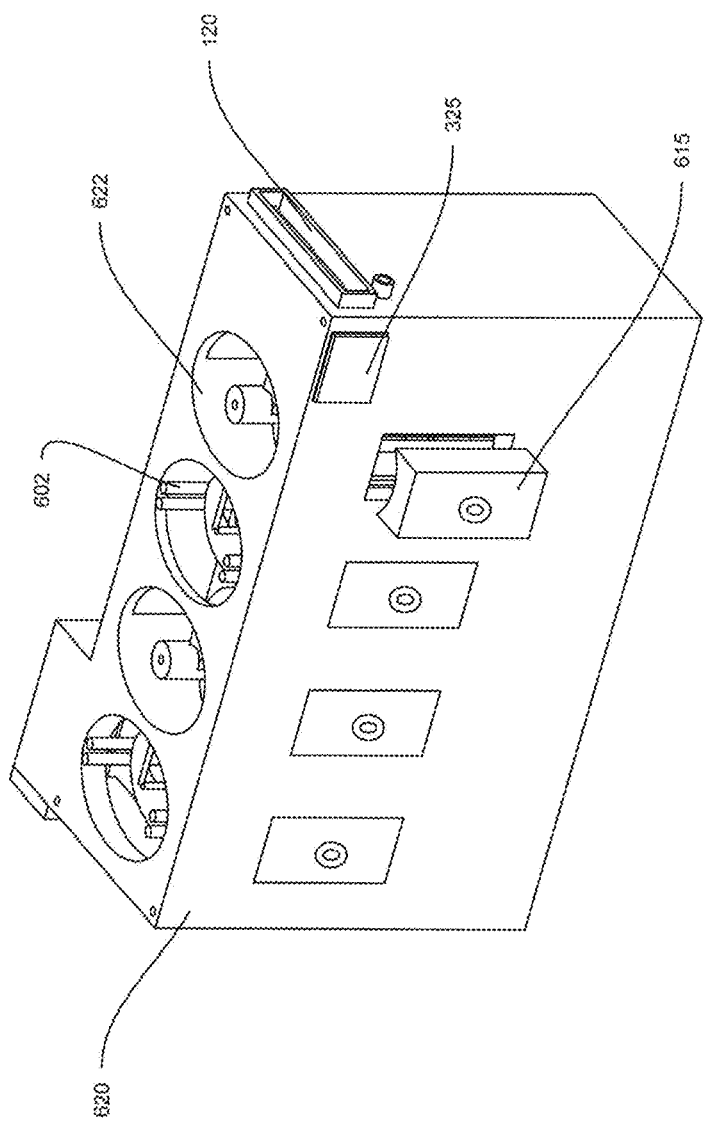
Figure 6M:
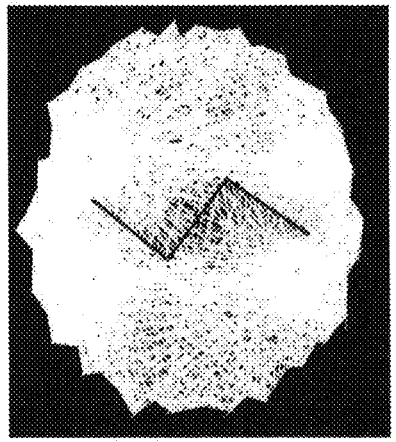
Figure 6L:
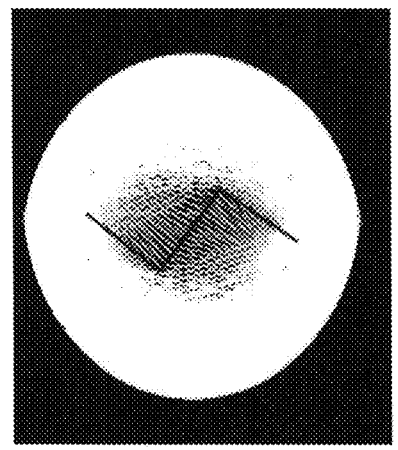

An alternate embodiment of the inner box 620 is illustrated in FIGS. 6F-6H. This embodiment is very similar to 6C except for the fact that the spaces between the disinfection chambers are solid and can be transparent/opaque. This will force the air to take the helical and serpentine path in close proximity to the UV-C sources without any leakage of air into dead spaces. Inner box 620 is a solid block configured to house a plurality of oval UV-C disinfectant chambers 622 equivalent to 610 as disclosed in FIGS. 6B, 6C and 6D. Each disinfectant chamber has a removable inspection window 615 to assist in the maintenance of the internal components of the inner box 620. The disinfectant chamber 622 contains a number of UV-C light sources 602 and a helical airflow diverter 608. The internal surface of the oval chamber wall 624 may be smooth or rough, but is preferably a rough crenulated surface 625 as shown in FIG. 6I. Typically the rougher the surface is, the more angular reflective angles it contains as seen in FIGS. 6J-6M. For example, the less crenulated angular internal surface shown in FIGS. 6J and 6K reflects the UV-C light rays 626 fewer times than a more crenulated angular surface as shown in FIGS. 6K and 6M.

When the inner box 620 is in use, air flow enters the inlet 120 and passes through a HEPA filter 325 before it enters the first disinfection chamber 622. The disinfection chambers 622 are connected alternately on the top air passage 680 and the bottom air passage 681 so that the air has to travel the full length of all the chambers in a zig-zag and serpentine pathway. Each of these chambers contains UV-C tubes/LEDs along the outer edges of the oval with circular helical devices in the center. This further reduces the dead space in the inner box and forces the organisms/harmful agents in the air to have a prolonged, direct, close contact to the UV-C radiation. Optionally the oval chambers are lined with reflective material and titanium dioxide to concentrate the UV-C and also to make the device more lethal to the offending agent. The reflective and titanium dioxide coatings can be one layer over the other or the coatings can be in alternate up and down full length longitudinal strips along the internal surface of the oval chamber wall, and any other available internal space.

Air Distribution Units

Mask Ventilator

The air distribution unit 170 distributes the purified and disinfected air exiting from the outer box 110 to the user of the apparatus or from 650 when only an inner box is needed. The air that has been filtered and disinfected in the box 140 is transported inside the outer box 110 and pumped out to an outlet/exit to the user. A couple of examples of suitable air distribution devices are face masks and endotracheal tubes used in conjunction with ventilators. In the case of an endotracheal tube 402 being the air distribution unit, the disinfection box 650 is directly connected to the air distribution, since the ventilator part the other units enclosed in the outer box 110 of the apparatus 100.

Other embodiments of the air distribution device 170 include electronic components; therefore the housing 110 may have a battery 182 as the power source 180 and a printed circuit board (PCB) 295/316 enclosed in enclosure 317 in electronic communication with any such electronic components. For example, a soft tube, such as, tube 220A or tube 220B (as shown in FIG. 2G) coupled to an electric cable 222. This electric cable allows the transfer of electric power to the mask, as well as for electric signal to/from an electric device in the mask, such as, a microphone 518, ambient light 573 and miniature pumps 330.

Endotracheal Tube and Conventional Ventilators. The air purification and disinfection box 650 can be incorporated into a mechanical ventilator to disinfect and purify the air going back to an individual patient. The inner box 140 of the original outer box 110 becomes the outer box 650 of the modified apparatus 100. A ventilator is a machine that provides mechanical ventilation by moving breathable air into and out of the lungs to deliver breaths to a patient who is physically unable to breathe or is breathing insufficiently. Ventilators are computerized microprocessor-controlled machines, but patients can also be ventilated with a simple, hand-operated bag valve mask. Ventilators are chiefly used in intensive-care medicine, home care, and emergency medicine (as standalone units) and in anaesthesiology (as a component of an anaesthesia machine).

A conventional ventilator 400 (see FIG. 4A) generally carries a patient's exhaled air away from the patient through tubing 405, conditions the air, and delivers the conditioned air (or air with increased oxygen) back to the patient through tubing 401 to an endotracheal tube 402 or a facial mask. When an air purification and disinfection box 650 is incorporated into the air flow passing through a ventilator as seen in FIGS. 4B-4J, the disinfection box 650 can disinfect, purify and/or condition the airflow.

Figure 4A:
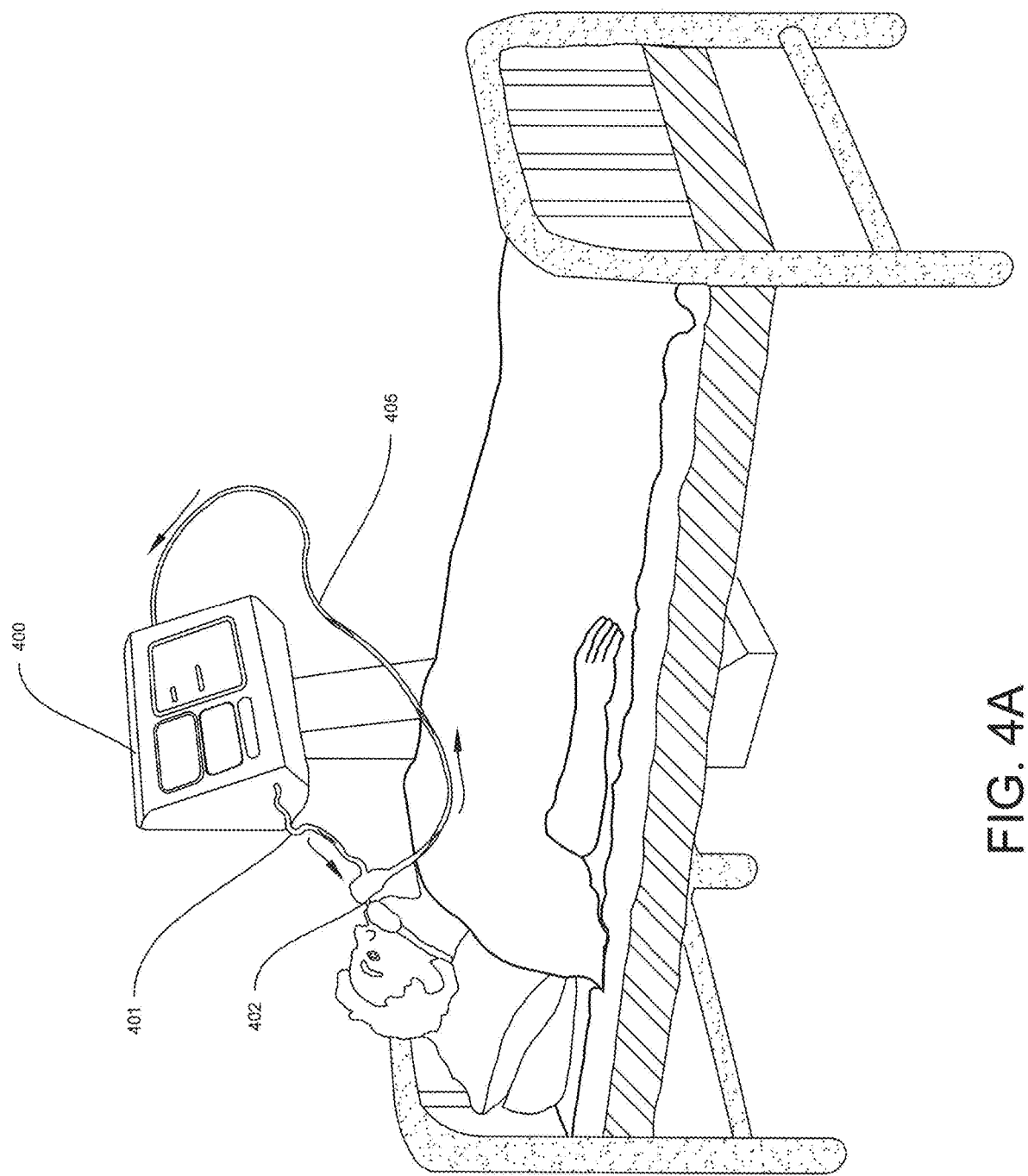
Figure 4B:
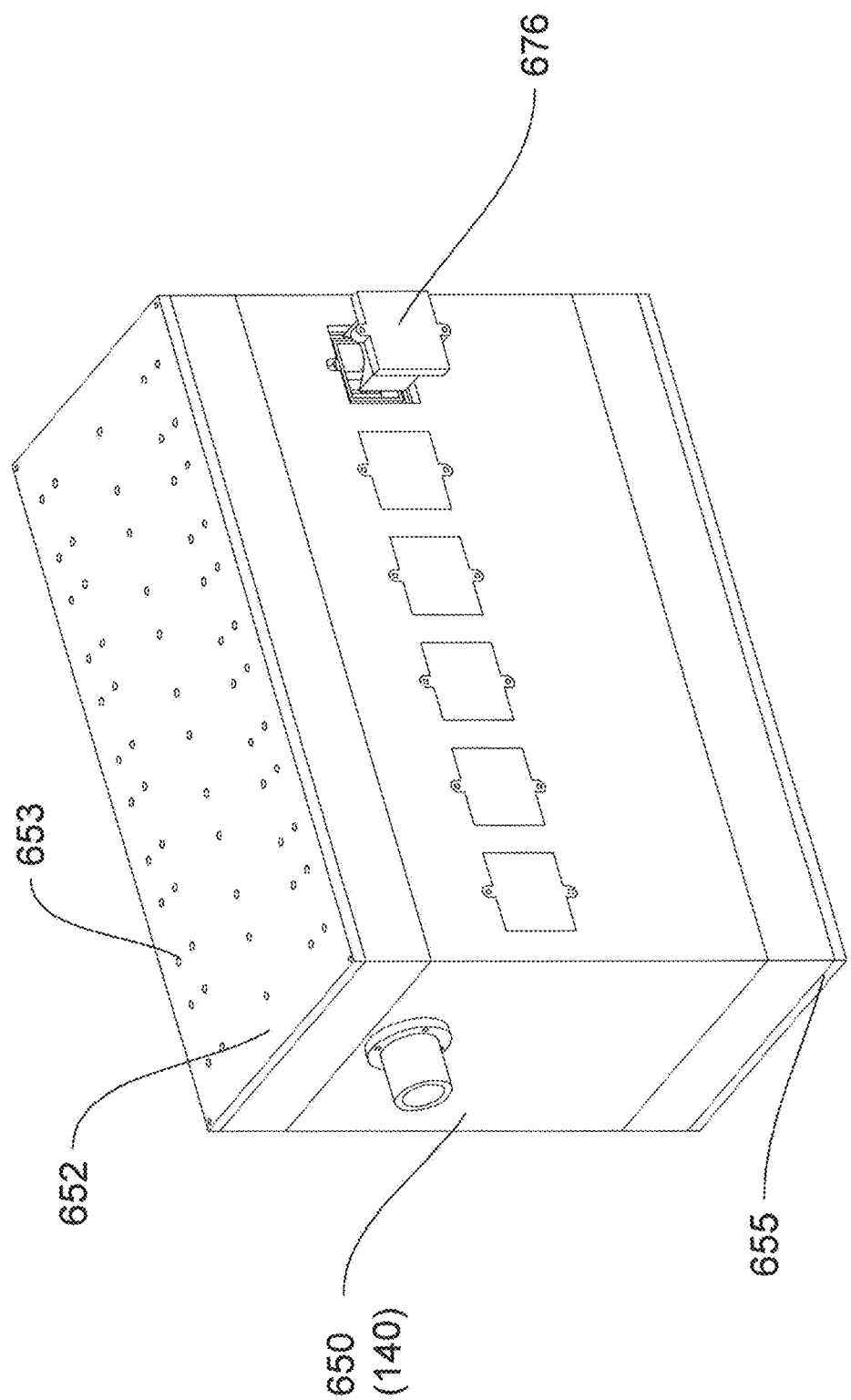
Figure 4C:
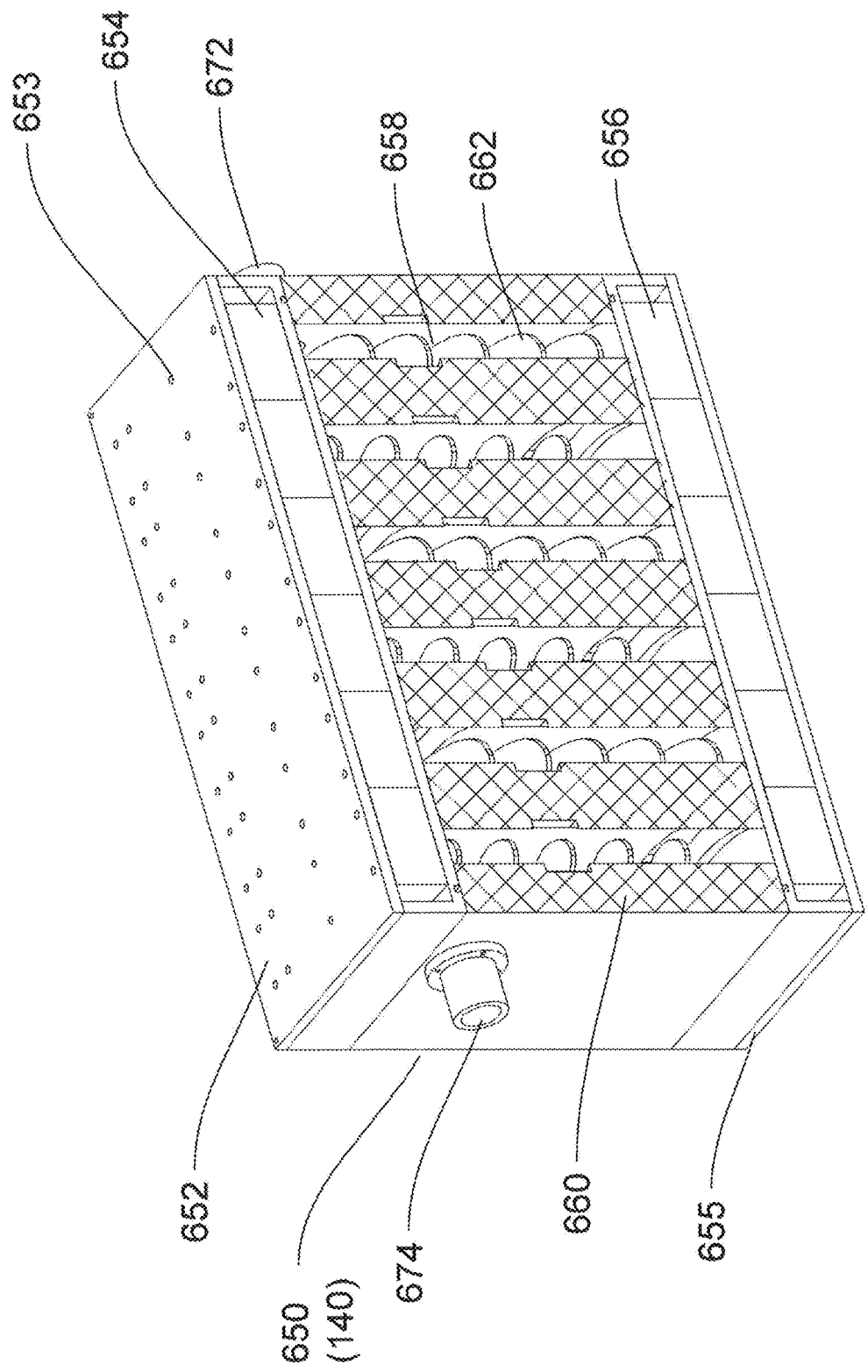

Modified Unit 100. One embodiment of the apparatus incorporates a "modified unit 100" that utilizes only the inner box of apparatus. The original system 100 has an inner box 140/600/315 enclosed in an outer box 110 to accommodate the filters and a pump. The conventional ventilators already have them and the apparatus needed here is only the inner box of the original system 100 which can be incorporated into the ventilator air flow as seen in FIGS. 4B-4C. The apparatus shown in FIGS. 4B-4C includes an outer box 650 which in reality is equivalent to the inner box 140, having a top lid 652, a bottom lid 655, a removable inlet spout 672, and a removable outlet spout 674. The top lid 652 has a number of holes 653 that allow the transfer of heat from one or more heat sinks to the outside air. The top lid also encloses the top ballasts 654. Similarly, the bottom lid encloses the bottom ballasts 656. The interior of the outer box 650 is similar to one of the other inner box embodiments already described and is configured to house a plurality of UV-C tubes in UV-C compartments 658. Typically each compartment 658 contains a UV-C tube and a helical airflow diverter 662. The compartments 658 are separated from each other by dividers 660. The groups of the UV-C tubes lie between two adjacent dividers 660 (thereby making up a disinfection chamber or compartment). Alternately the structure may be similar to 6H. The compartments with their UV-C lights and helical airflow diverter 662 irradiate the air flowing through the compartment in a helical manner. The outer box may optionally include inspection windows 476 that may be used to monitor the operation and viability of the components of the compartments 658.

Figure 4D:
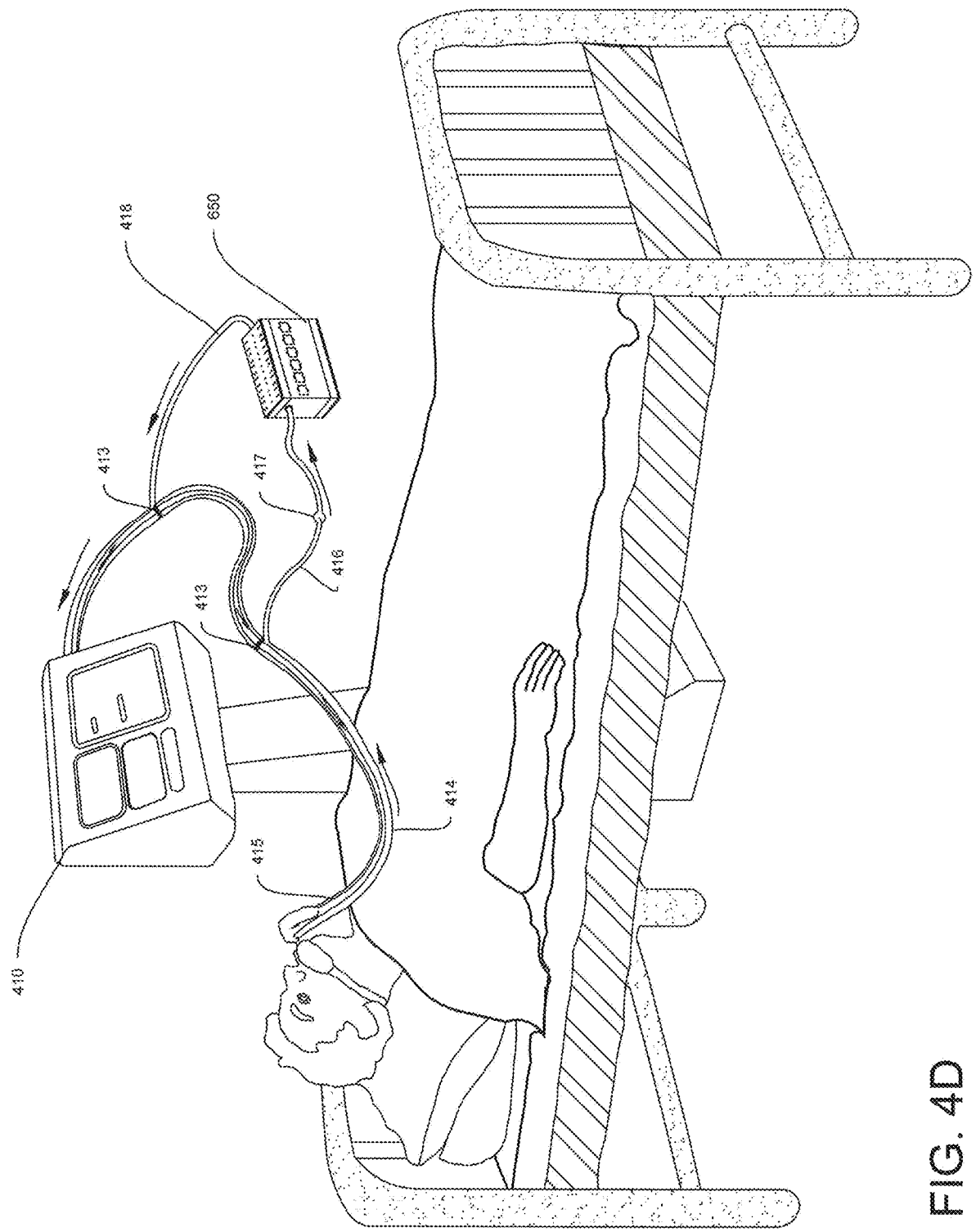

FIG. 4D illustrates an embodiment that incorporates the disinfection box 650 into the ventilator 410 air flow. In this embodiment, an exhaled air line 414 goes from the patient to a flow diverter 413, where the exhaled air is diverted into air line 416. The diverted air flow goes through a one directional valve 417 into the disinfection box 650. The purified, disinfected air that exits the apparatus is sent to the ventilator 410 via tubing 418. The oxygenated, purified, and disinfected air exiting the ventilator is sent back to the patient through tubing 415.

Figure 4E:
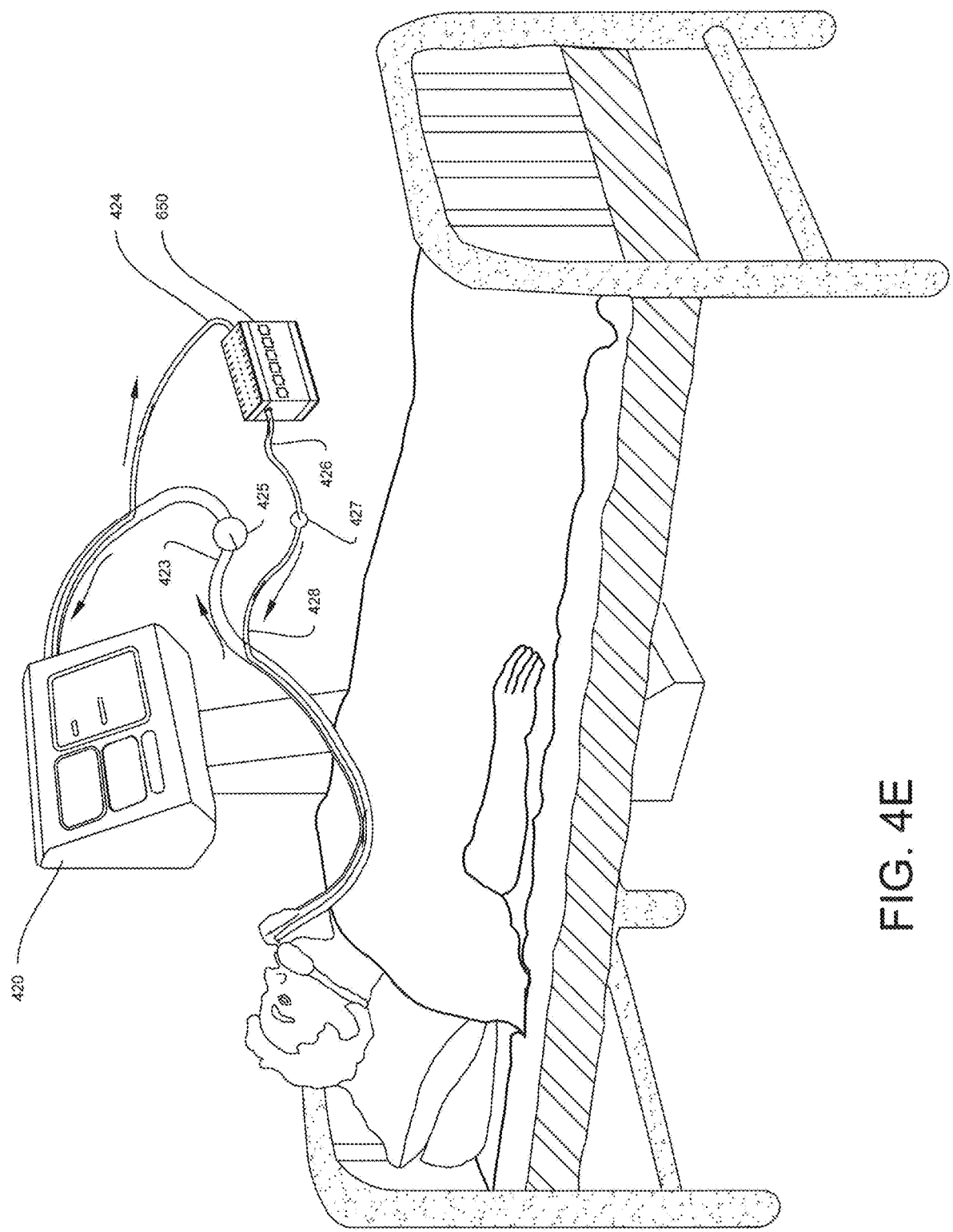

FIG. 4E illustrates a second embodiment of incorporating the disinfection box 650 into the ventilator 420 air flow. In this embodiment, exhaled air from the patient passes through air line 423, through a one directional valve 425, and into the ventilator 420. Oxygenated air from the ventilator is sent via tubing 424 to the disinfection box 650 for purification and disinfection. The oxygenated, purified, and disinfected air flow from the apparatus then flows through tubing 426, through a one directional valve 427, and returned to the patient through tubing 428.

Figure 4F:
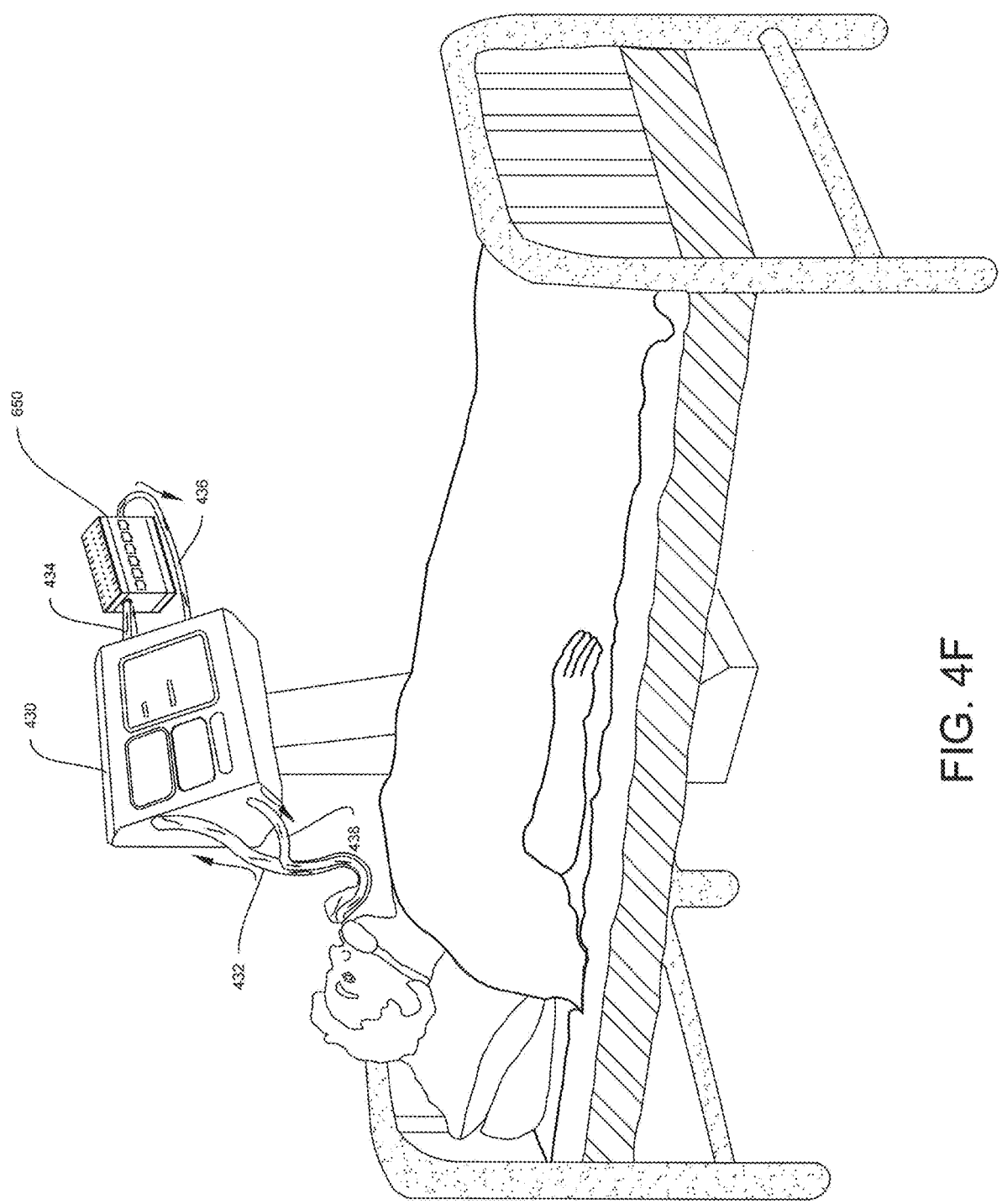

FIG. 4F illustrates a third embodiment for incorporating the disinfection box 650 into the ventilator 430 air flow. Tubing 432 carries the patient's exhaled air to the ventilator 430 where it is oxygenated. The oxygenated air flow is sent to the disinfection box 650 through tubing 434 and then back through tubing 436 to the ventilator 430. The oxygenated, purified, and disinfected air flow is returned back to the patient through tubing 438.

Figure 4G:
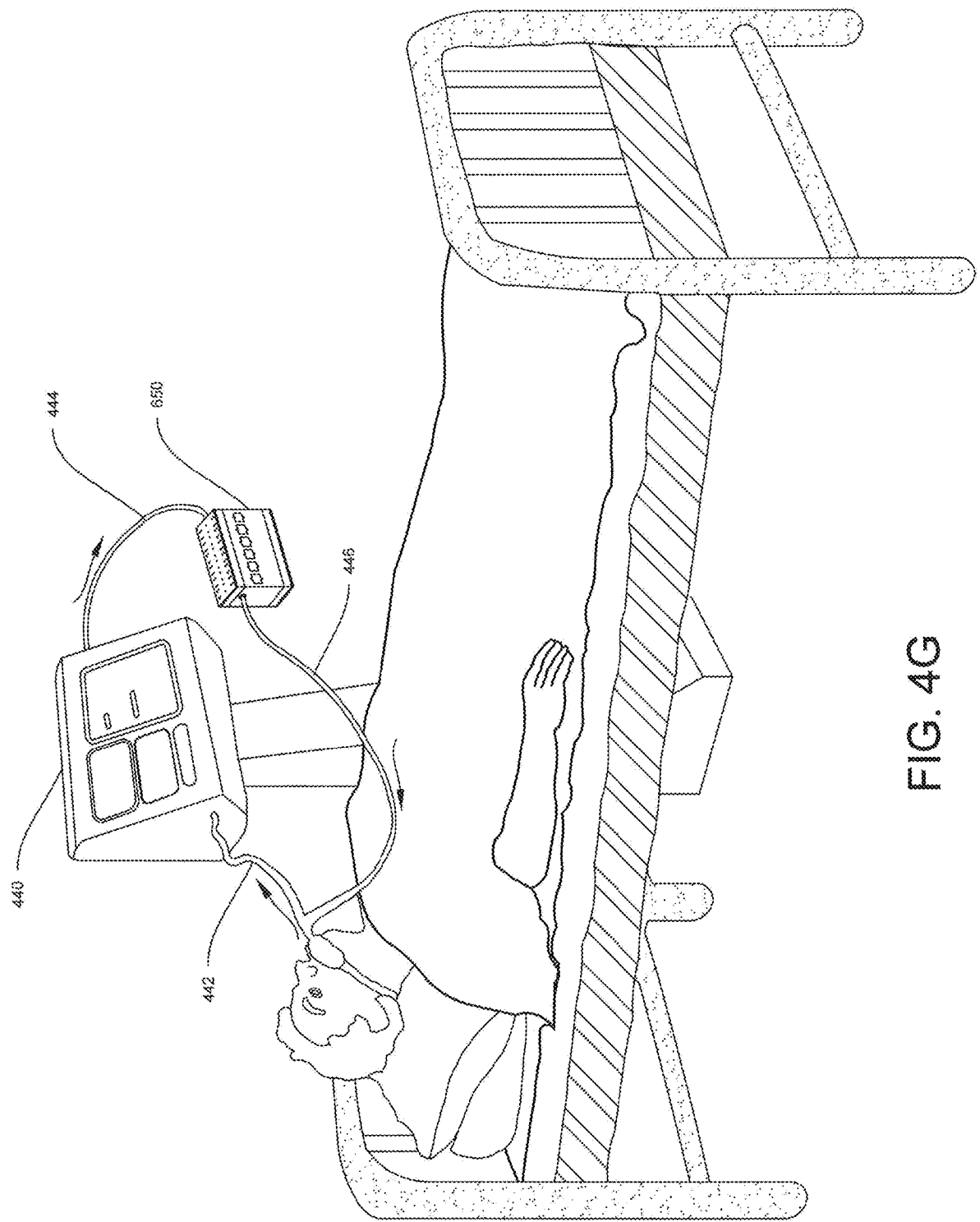

FIG. 4G illustrates a fourth embodiment for incorporating the disinfection box 650 into the ventilator 440 air flow. Tubing 442 carries the patient's exhaled air to the ventilator 440 where it is oxygenated. The oxygenated air flow is sent to the disinfection box 650 through tubing 444 and then the oxygenated, purified, and disinfected air flow is returned back to the patient through tubing 446.

Figure 4H:
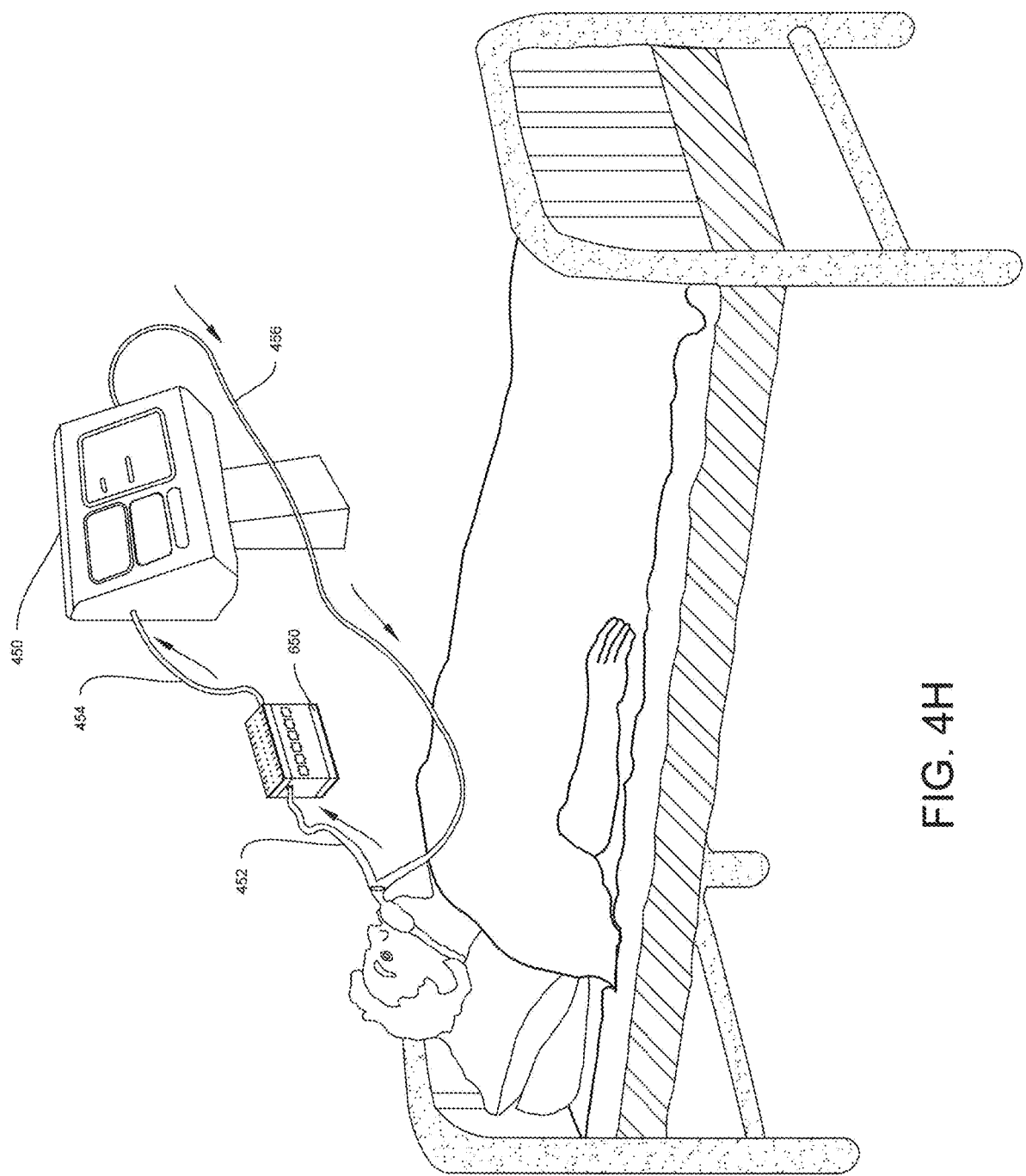
Figure 41:
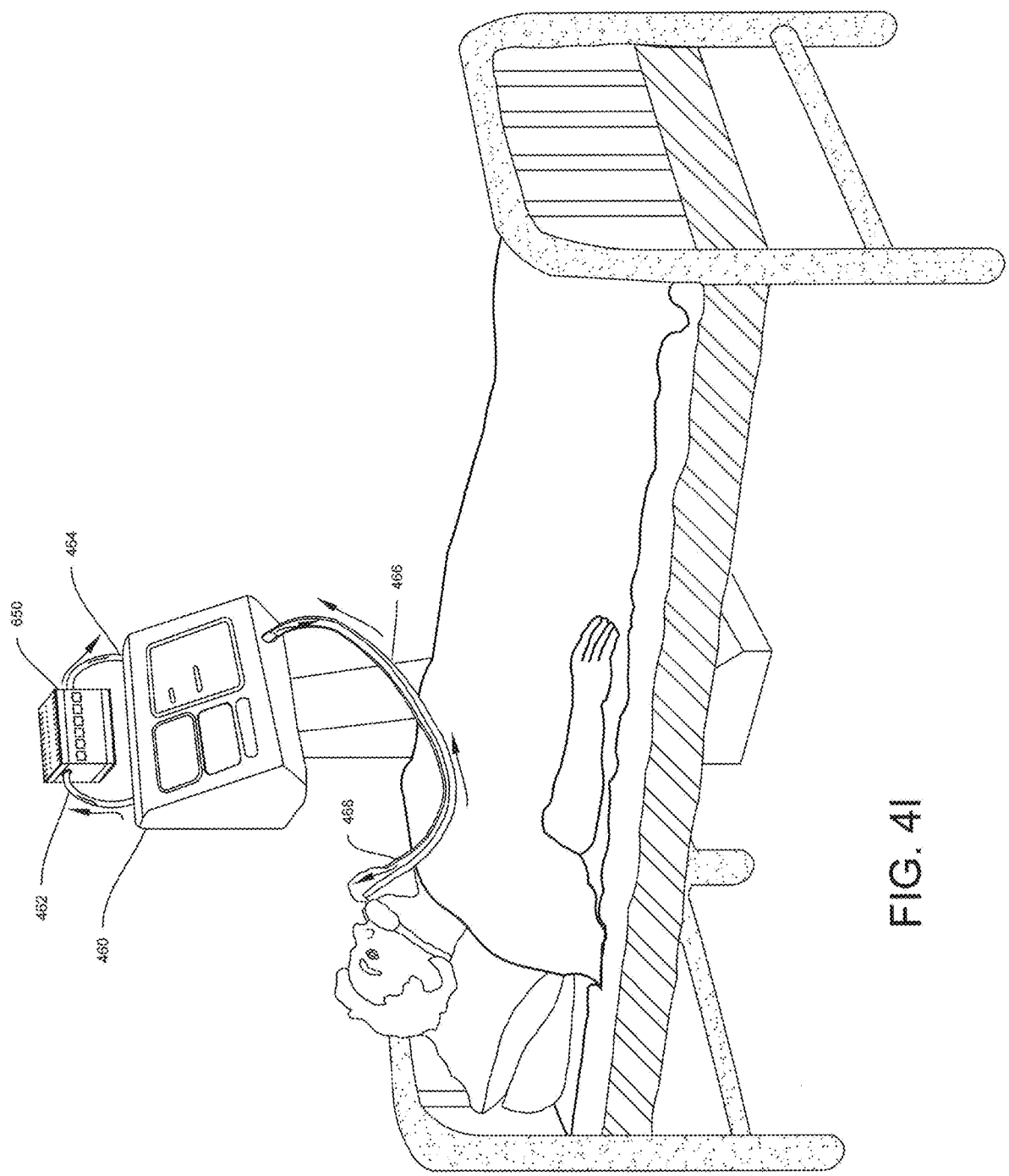

FIG. 4H illustrates a fifth embodiment for incorporating the disinfection box 650 into the ventilator 450 air flow. Tubing 452 carries the patient's exhaled air to the disinfection box 650, once the air is purified and disinfected it is sent to the ventilator 450 where it is oxygenated via tubing 454. The oxygenated, purified, and disinfected air flow is returned back to the patient through tubing 456.

FIG. 4I illustrates a sixth embodiment for incorporating the disinfection box 650 into the ventilator 460 air flow. Tubing 466 carries the patient's exhaled air to the ventilator 460. Tubing 462 carries the patient's exhaled air from the ventilator to the disinfection box 650. Once the air is purified and disinfected, it is returned to the ventilator 460 where it is oxygenated via tubing 464. The oxygenated, purified, and disinfected air flow is returned back to the patient through tubing 468.

Figure 4J:
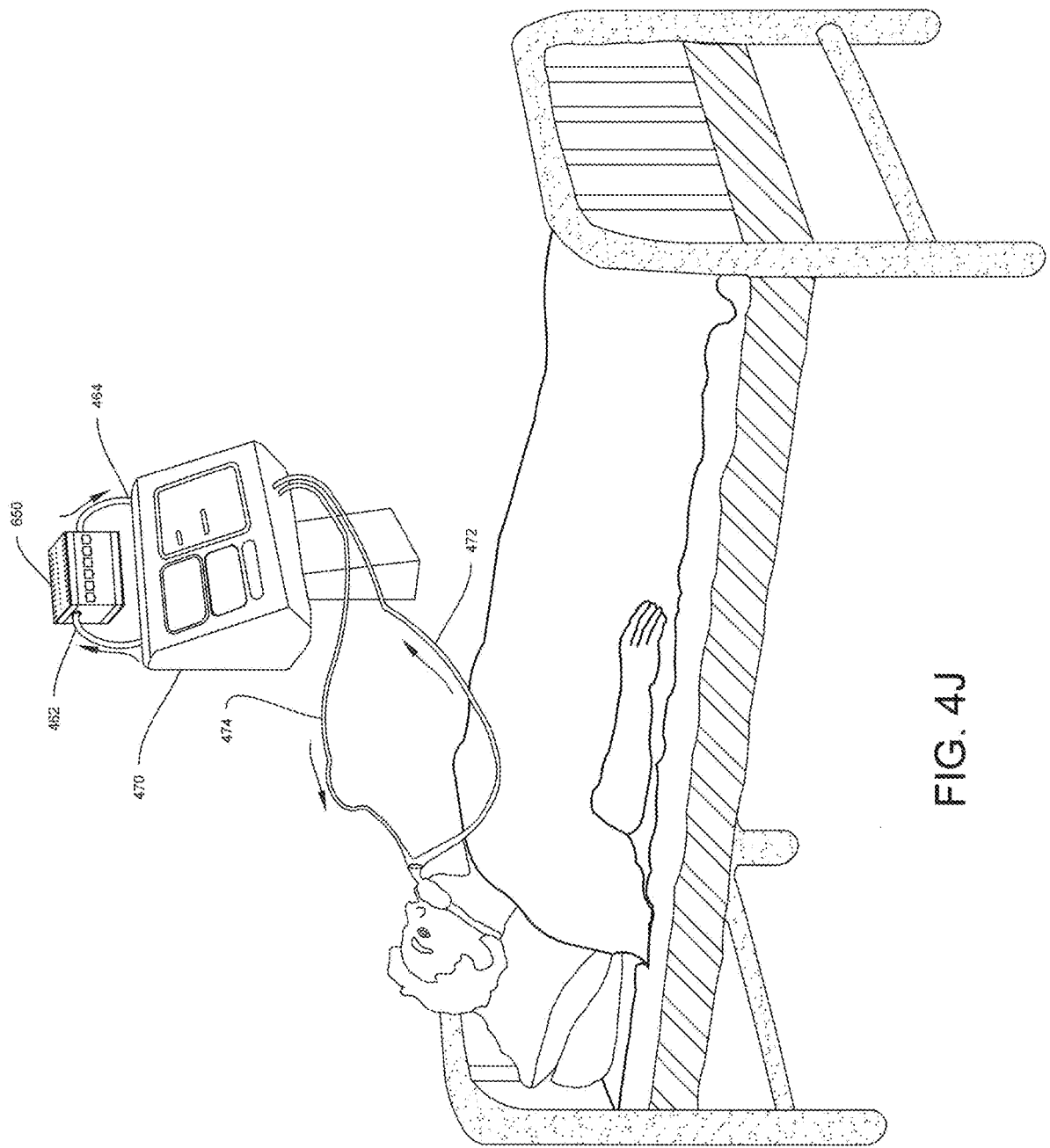

FIG. 4J illustrates a seventh embodiment for incorporating the disinfection box 650 into the ventilator 470 air flow. Tubing 472 carries the patient's exhaled air to the ventilator 470. The exhaled air is oxygenated and purified and then returned to the patient through tubing 474.

Figure 4K:
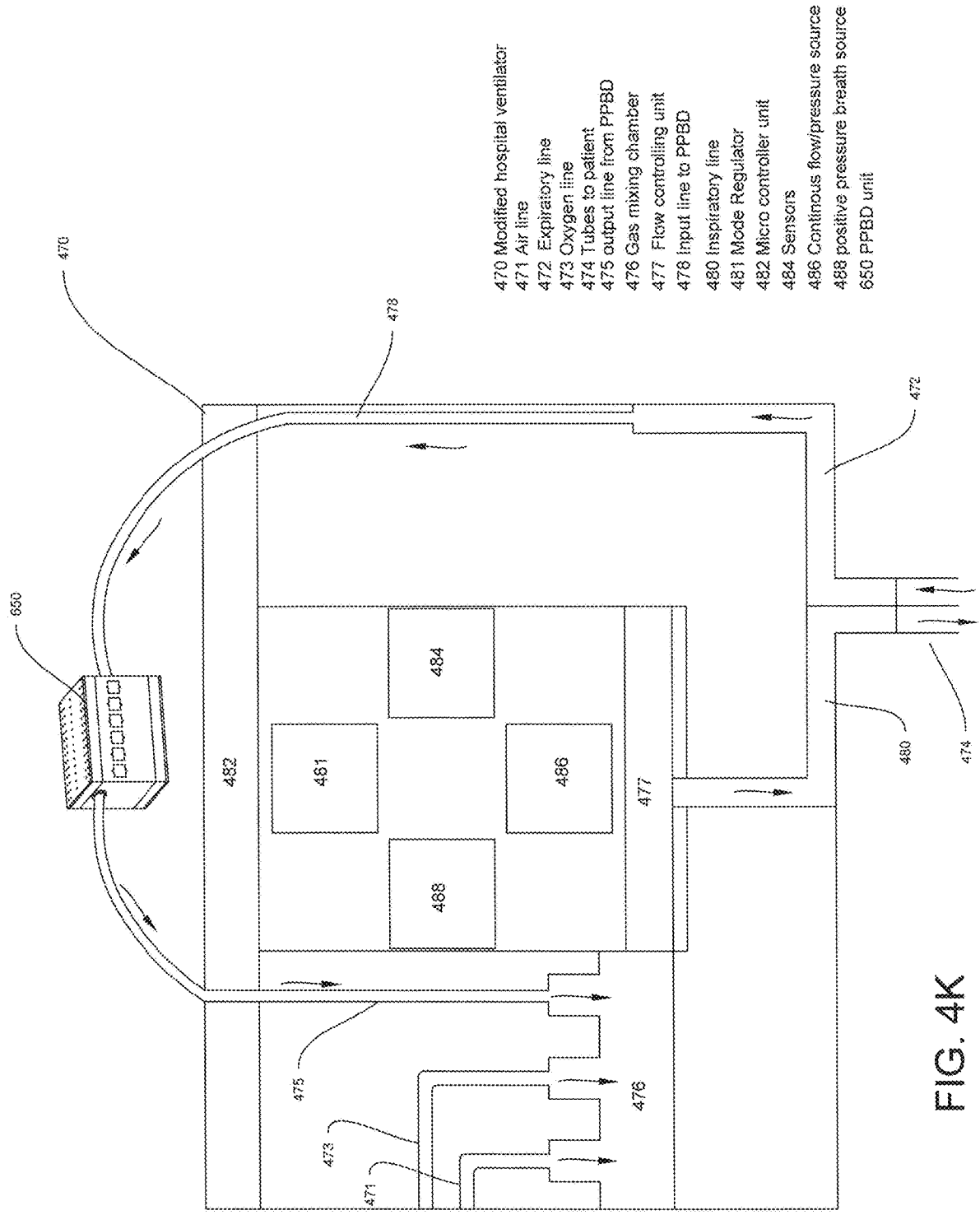

FIG. 4K is a more detailed illustration of how the disinfection box 650 interacts with the ventilator 470 in the seventh embodiment. The ventilator's access 480 allows the patient's exhalations to enter the ventilator through tubing 472. Tubing 472 is connected to input tubing 478 that delivers the patient's exhalations to the disinfection box 650 where they are purified and disinfected. The purified and disinfected patient's exhalations are delivered via tubing 475 to a gas mixing chamber 476. The gas mixing chamber 476 further conditions the purified and disinfected patient's exhalations by mixing them with ambient air delivered through tubing 471 and oxygen delivered through tubing 473. The flow rate of the air source through the disinfection box 650 and the mixture chamber 476 is controlled by a flow controlling unit 477. The purified, disinfected, and conditioned air is returned to the patient via tubing 474. Other operational controllers for the ventilator 470 are the microcontroller unit 482, various sensors 484, the mode regulator 481, and a positive pressure breath source 488. A person skilled in the art will recognize that many configurations of the ventilator 470 and its components can be made to enhance certain patient goals. Furthermore, it would be obvious to one skilled in the art that the modified ventilator 470 can have fewer or more components that shown in FIG. 4K and described above.

Figure 5A:
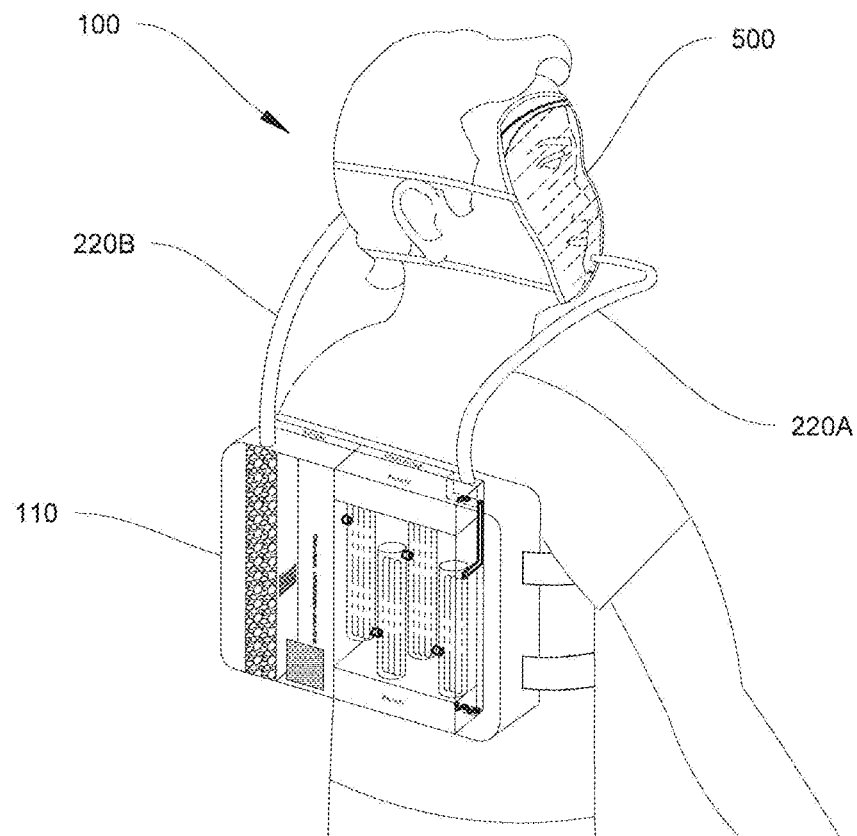
FIG. 5A illustrates an exemplary portable air purification and disinfection system and a sealable full face transparent mask.

Face Masks and Mask Ventilators. Exemplary examples of face masks as air distribution units 170 are illustrated in FIGS. 1B, 5A and 5E. FIGS. 1B, 5A and 5D exemplify face masks that can be personally transported using a back pack or a briefcase.

For example, FIG. 5A illustrates an embodiment of a transparent, air tight sealable, full face mask 500 connected exclusively to the housing 110 and disinfection chamber shown in FIG. 2B. Unlike the conventional face masks there is no air movement between the outside air and the air inside the mask except the air coming exclusively from the apparatus. The face mask 500 is configured to circulate a user's exhaled air to the disinfection chamber via tubing 220B where it is purified and disinfected before it is sent back to the user wearing face mask 500 via tubing 220A.

Figure 5B:
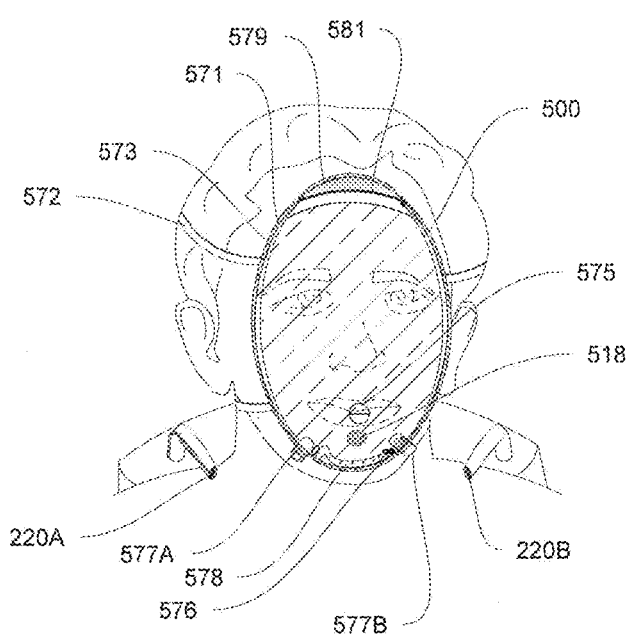
Figure 5C:
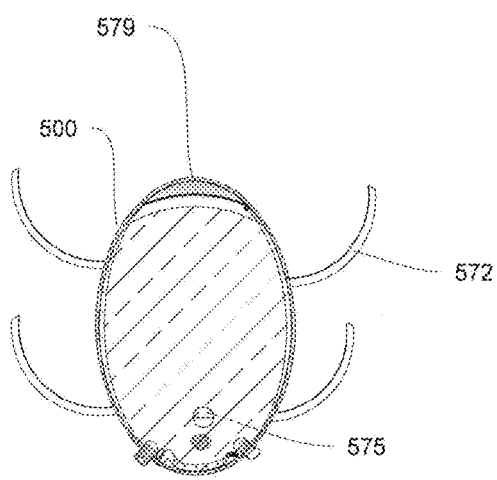
Figure 5D:
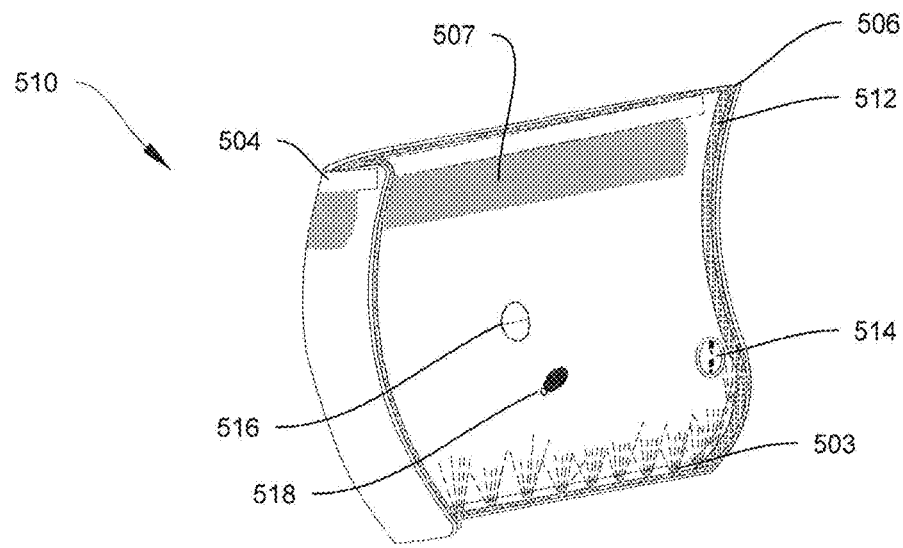
FIGS. 5D and 5E illustrate one embodiment of a half face mask.
Figure 5E:
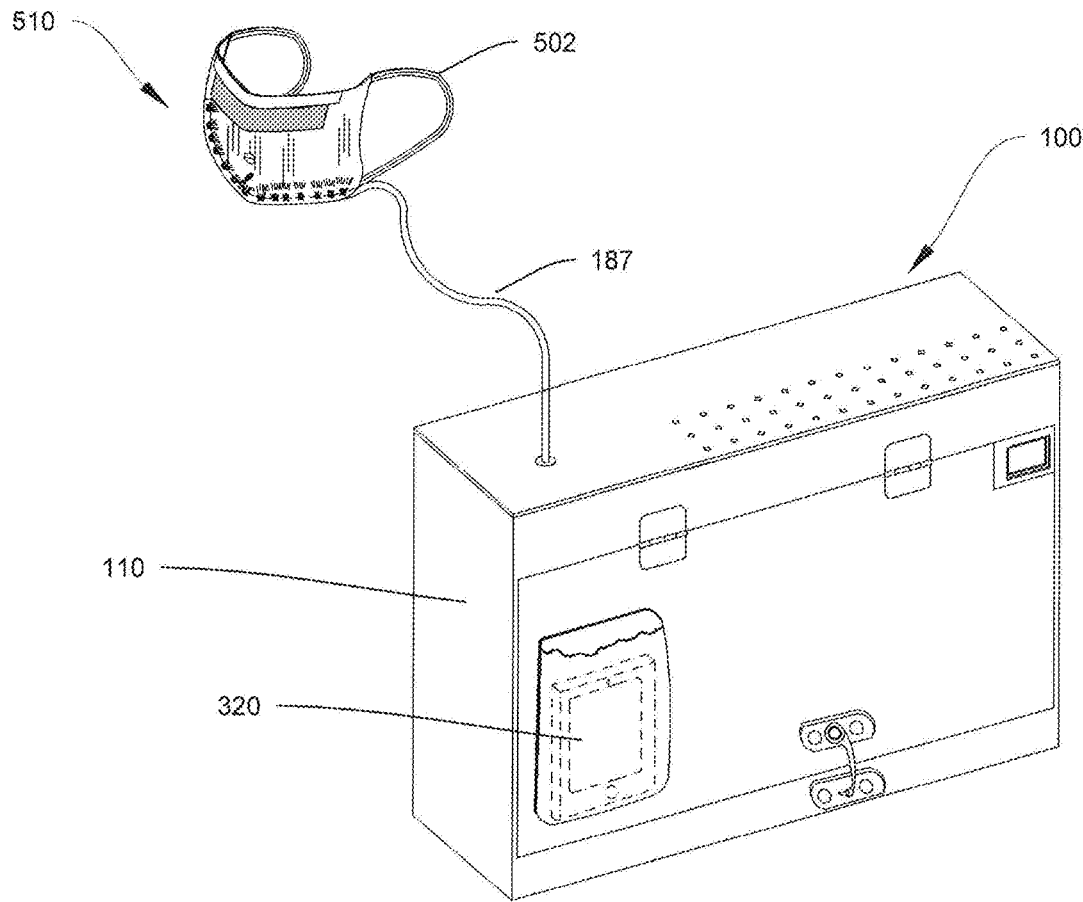

FIGS. 5B and 5C show more details of the face mask 500. The mask 500 can optionally include an ambient light source 573, a microphone 518, and an opening 575 to insert a straw. A fan 576 on the face mask 500 can be coupled to the wearable air purification and disinfection apparatus 100 shown in FIG. 5A. The edges of the mask 500 can be fitted below the hairline, in front of the ears and below the chin. The mask 500 can have an air-filled collapsible tube 571 along its circumference. The mask can be held in place through one or more fasteners 572. For instance, the fastener 572 can include elastic bands, belts, or straps fastened using a hook and loop fastening mechanism (such as, Velcro). The fastener 572 and the collapsible air tube 571 along the circumference of the mask can ensure that the mask 500 can be worn in an airtight manner, complimented by the air pressure inside the mask.

The mask 500 can further have an air inlet port and an air exit/outlet port. The exit port 577B includes a screw spout which can be coupled with one end of a soft tube 220B which has receiver screw threads inside on both ends. The inlet port 577A is similar to the exit port and has a spout for the incoming air through soft tube 220A. These ports can be located at the bottom left and right sides of the mask. An opening 575, that may optionally have a selectably sealable elastomeric cover, can be positioned in the middle of the mask 500, towards the bottom surface. The elastomeric cover is configured to keep the opening closed when not in use. A straw or a spout (or any such sipping/drinking means) can be inserted through this opening 575 for the user of the mask 500 to drink liquids, such as water, coffee or any other beverage, and even pureed food.

The air coming through the inlet of the mask 500 can be released into the mask through a long tube 578 located proximal to the lower edge of the mask. The tube 578 includes multiple holes/openings so that the air flow is directed from bottom up. A small vertical separation (not shown) can be provided to prevent the air going directly into the exit port. When the exit port is closed, air will go all the way up to the top of the mask 500. An elongated N95 or N95-type filter sheet 579 is positioned along the width of the top edge of the mask 500. The sheet 579 is configured to filter out all types of particulates such that the air exiting the mask 500 is substantially clean. This sheet 579 is secured in position and enclosed with a zipper arrangement 581. The zipper can be closed in patients having virus in their exhaled air so that their exhaled air is not released outside. Instead the air goes out through exit tube 577B back into the housing unit 110 to be purified and disinfected.

One or more miniaturized fans 576 can be placed along a lower edge of the mask 500. The fans 576 are configured to drive the air upwards and can also assist in defogging the mask 500. The fog can also be prevented by spraying or wiping the inside of the mask 500. The fans 576 can be turned on or off by the user to clean the mask. The fans 576 can have two or more speed options. Additionally, a very thin row of LED light sources 573 can be placed around the mask 500 such that there is just enough lighting to make the face visible through the mask.

FIGS. 5B, 5D and 5E illustrate embodiments of a half face mask. For example, FIG. 1B shows a half face mask 508 in communication with the air purification and disinfection apparatus 100. The face mask 508 may be transparent and sealable and takes air exclusively from the apparatus without any air coming directly from the outside air. In the half face mask 508 shown in FIG. 1B, the purified, disinfected air is delivered to the mask 508 via tubing 134 and the user's exhaled air is returned to the housing intake via tubing 136. More specifically, a first end of tubing 134 is connected to the wearable housing 110 while a second end of the tubing 134 is fitted within a first opening in a tight-fitting medical grade mask 508. The user can, therefore, be provided with substantially pure/disinfected air for inhalation and any virus from an infected person is not released to the outside air. Unlike with a regular surgical or N95 mask, these infected people are not forced to rebreathe their own viruses that they are trying to expel. Air that is exhaled by the user/wearer of the wearable housing 110 is routed from the mask 508 to the housing 110 by tubing 136. One end of the tubing 136 is fitted within a second opening in the mask 508 while a second end of tubing 136 is connected to a housing air inlet 120. The exhaled air is filtered to remove the carbon dioxide through a carbon dioxide filter and another HEPA filter and then mixed with the air/oxygen mixture in the outer box 110 and released to the inner box 140 containing the disinfection chambers. The filtered and disinfected air is again routed to the mask 508. For further protection, the user wearing the portable housing 110 can be air washed to remove any residual surface contamination before going into a change room. The entire system provides a substantially close circuit device to supply exclusively disinfected purified air to the individual. Optionally, when worn by the healthy individuals, the exit port can be left open and not connected to the chamber. The system including the enclosed pump and air-tight face mask can function as a portable mask ventilator.

Another embodiment of a half face mask 510 is shown in FIGS. 5D and 5E. FIG. 5D is an exemplary perspective view from the rear of a half face mask. The face mask 510 may be sealable and multipurpose. The face mask 510 may be a transparent like the face mask 500. The mask 510 is held tight over the face through elastic loops taken around the ears 502 or straps like the straps 572 on the mask 500. The mask 510 may further include LED lights 512 (also referred to as ambient LED and these terms are used interchangeably hereinafter) located around a periphery of the mask to light up the face of the user, a microphone 518, and a straw opening 516. The mask 510 may further include a metal clip 504 located on the top side that allows a user to fit the mask snugly around the nose, and a N95 filter 507 located below the metal clip 504 that can filter outgoing air to reduce the risk of the user releasing microorganisms, such as bacteria or viruses, into the air. The mask 510 can include a battery 514 to power the LED lights 512. A tube 187 can be arranged along the lower border of the mask to carry the incoming purified air from the housing and disinfection chamber to a plurality of holes 503 that can release air in an upward direction. The air stream from the holes 503 can defog the mask and thereby improve visibility. A collapsible tube 506 can be arranged around the mask to make it airtight.

Transport Carrier

Figure 7B:
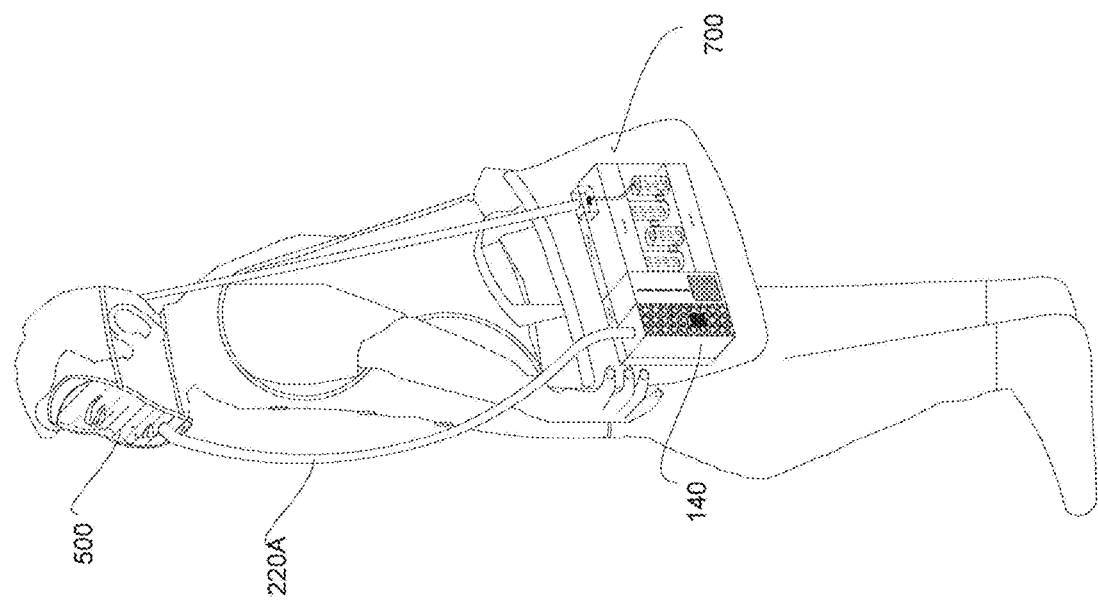
FIGS. 7A-7C illustrate several embodiments of a transport carrier for the air purification and disinfection system
Figure 7A:
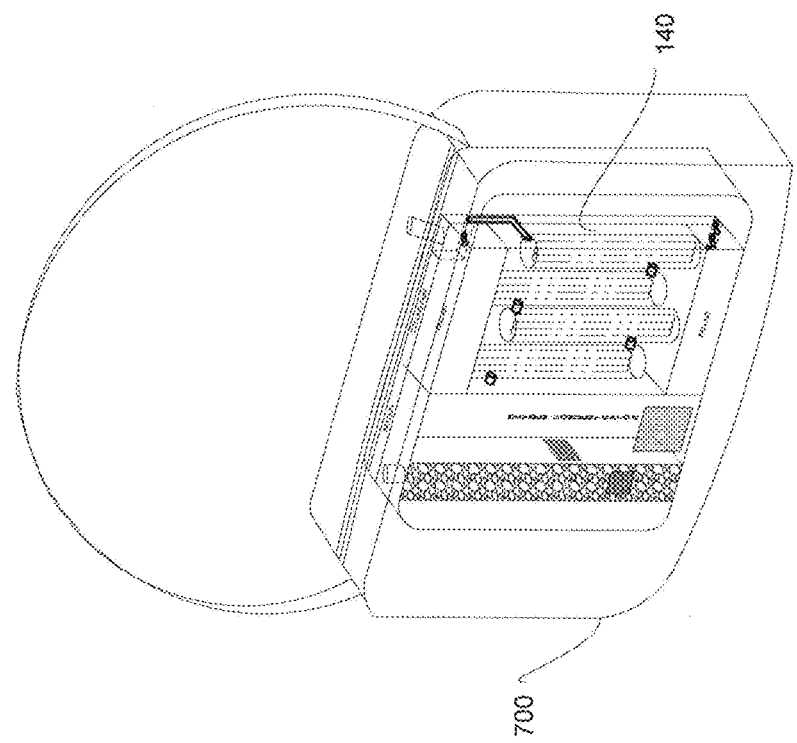
Figure 7D:
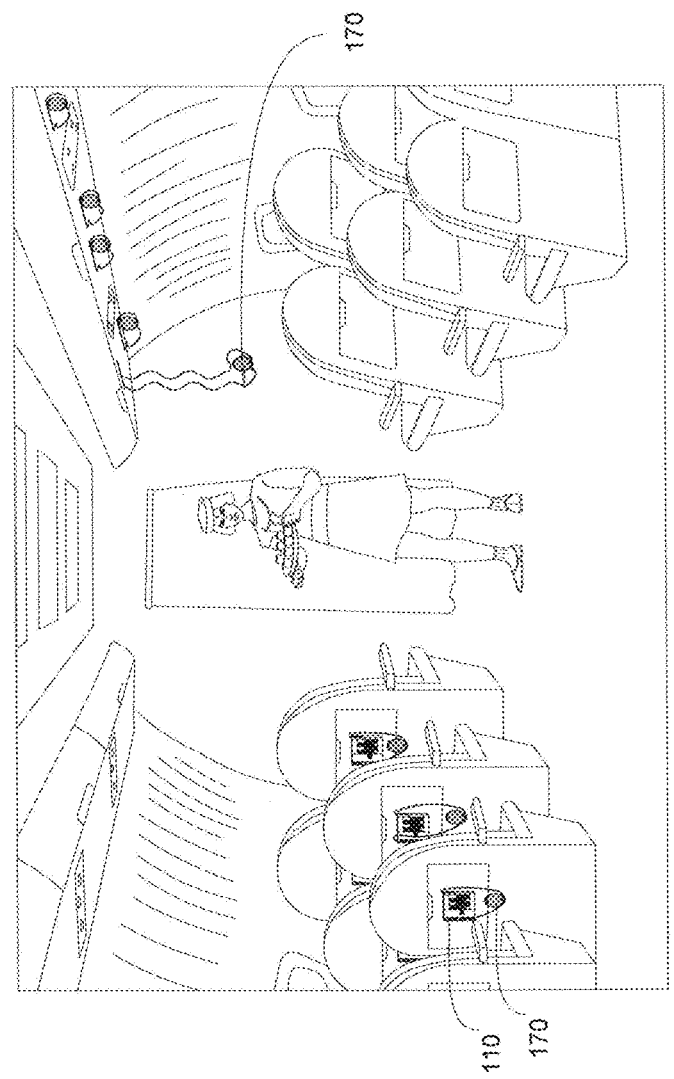
FIG. 7D illustrates the use of the personal air purification and disinfection system in an airplane.
Figure 7C:
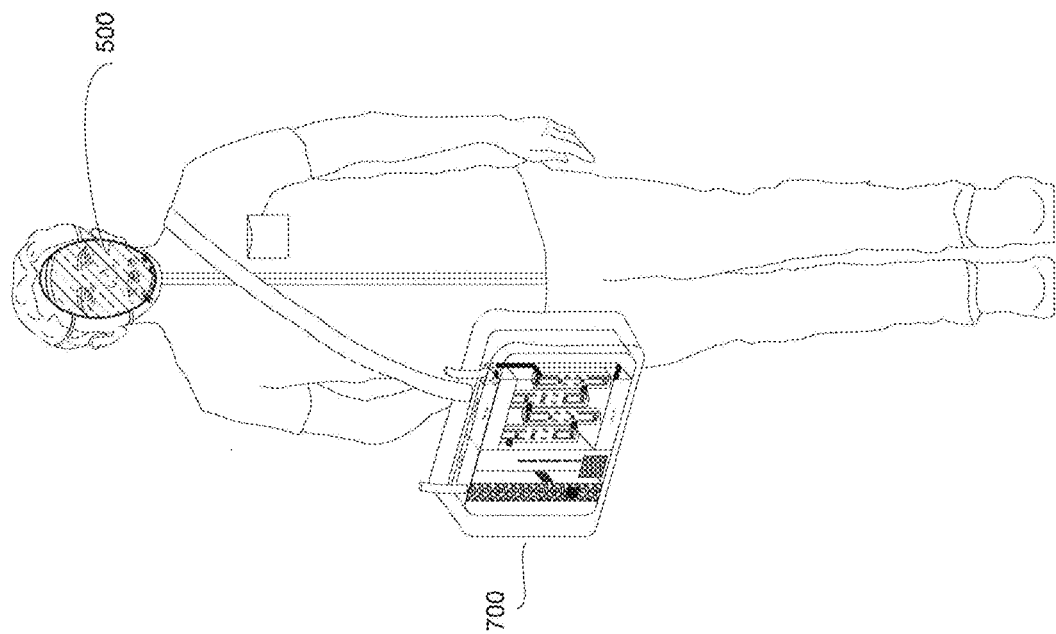
Figure 7E:
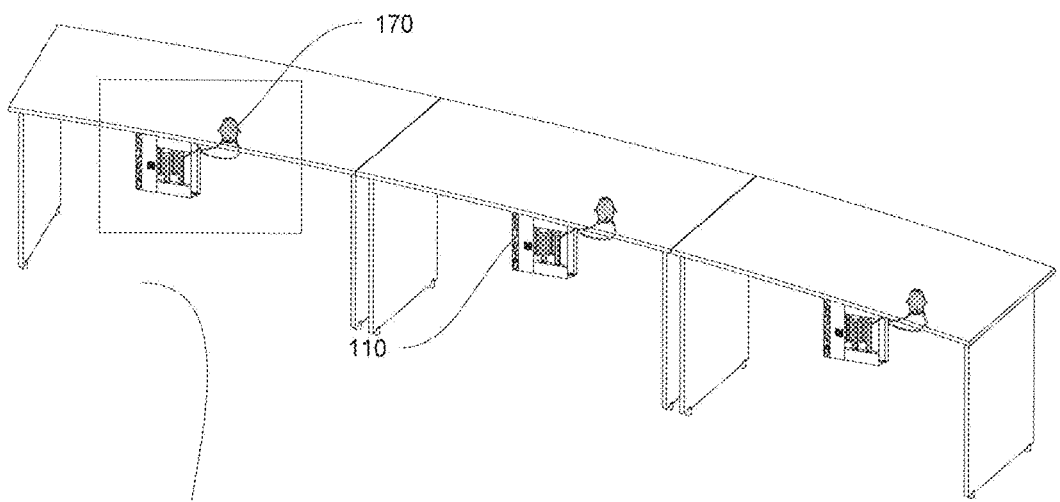
FIGS. 7E and 7F illustrate the use of the personal air purification and disinfection system in an office environment integrated with a desk/conference table, in accordance with an embodiment.
Figure 7F:
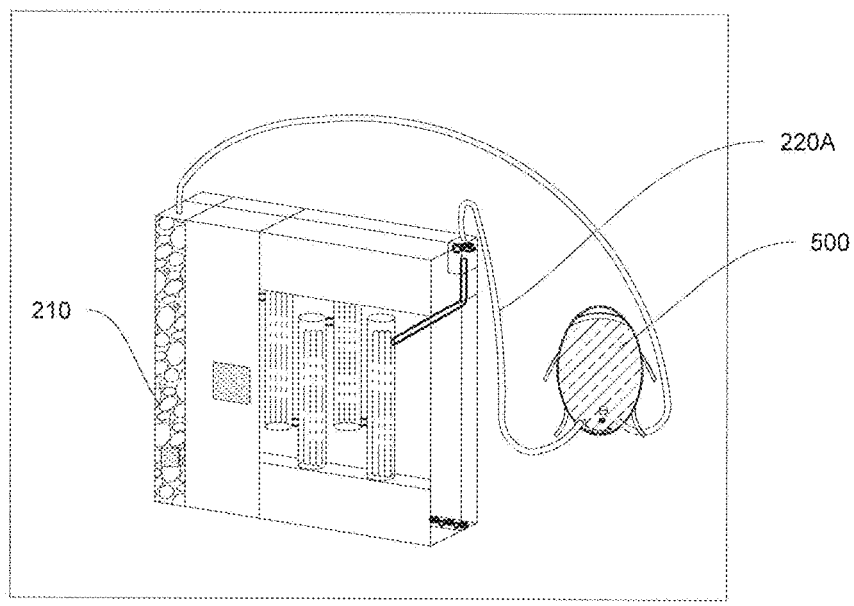

Some embodiments of the air purification and disinfection apparatus 100 are configured to be incorporated within a pre-existing space such as a room, or a desk (see FIG. 7E), an airplane overhead compartment or passenger seats (see FIG. 7D), or under a conference table. Even though used in open spaces, the units are meant for personal use and there will be one such unit per person.

Other embodiments of the air purification and disinfection apparatus 100 are configured to be mobile. For example, the air purification and disinfection apparatus 100 can be configured to be carried or worn by an individual. A transport carrier 700 can be used by an individual to carry their own air purification and disinfection apparatus 100 around with them. Several of the illustrated embodiments of the transport carrier 700 also serve as the housing 110 for the apparatus 100. For example, a transport carrier 700 can be a backpack (see FIGS. 1B and 5A) that can be conveniently worn by a user, such as, a healthcare worker, or any user who requires an uninterrupted supply of disinfected and purified air. Other embodiments of a transport carrier 700 are a purse or briefcase (see FIGS. 7A and 5E), a vest pack, a hip pack, a shoulder bag (see FIGS. 7B and 7C), or a cervical collar (see FIGS. 2E-2G).

FIGS. 2E-2G illustrate different embodiments where the housing 110 of the apparatus is configured as a cervical collar. The cervical collar can be worn around the neck of a user with the collar part positioned towards the back of the neck and any attachments positioned along the front or the sides of the user's neck. The purified, disinfected air from the cervical collar can be received by the user, for instance, through a first soft tube 220A which is connected to a first side of the cervical collar through a threaded outlet or out spout 227A. The air enters the collar from the second side through a second soft tube 220B connected to an inlet 227B to cervical collar. The two ends of the opening 272 to the collar are configured to encircle the neck of the user. The cervical collar (or the other embodiments of the wearable device disclosed herein) can serve as the housing 110 or they can be further coated with or enclosed within an UV-C opaque material to control UV-C light leakage. The cervical collar opening 272 can be configured to be flexible or made in a plurality of sizes depending on the user's neck size. For example, it can be manufactured in small, medium and large sizes.

Power Source

The air purification and disinfection apparatus 100 is connectable to a power source. The apparatus 100 may have a plug that will plug the apparatus into an electrical system or the apparatus 100 may have a compartment to hold or contain a power source 180. The compartment can accept one or more power sources 180. The power source is often one or more batteries 182 which are generally removable and replaceable from the apparatus 100.

The power source 180 can include batteries 182 that can be recharged and/or replaced, to meet the power requirements of the apparatus 100. Such batteries can be lithium ion, nickel cadmium, nickel-metal hybrid, alkaline or any other type of batteries.

User Interface

The operation of the air purification and disinfection apparatus 100 in medical facilities such as intensive care units will typically be controlled using a computer program application (not shown) installed on a computer device. In other embodiments, the air purification and disinfection apparatus 100 can be operated using a computer program application (not shown) on a portable smart device, such as, a mobile phone. In yet other embodiments, the air purification and disinfection apparatus 100 can be controlled using a controller device.

Figure 8:
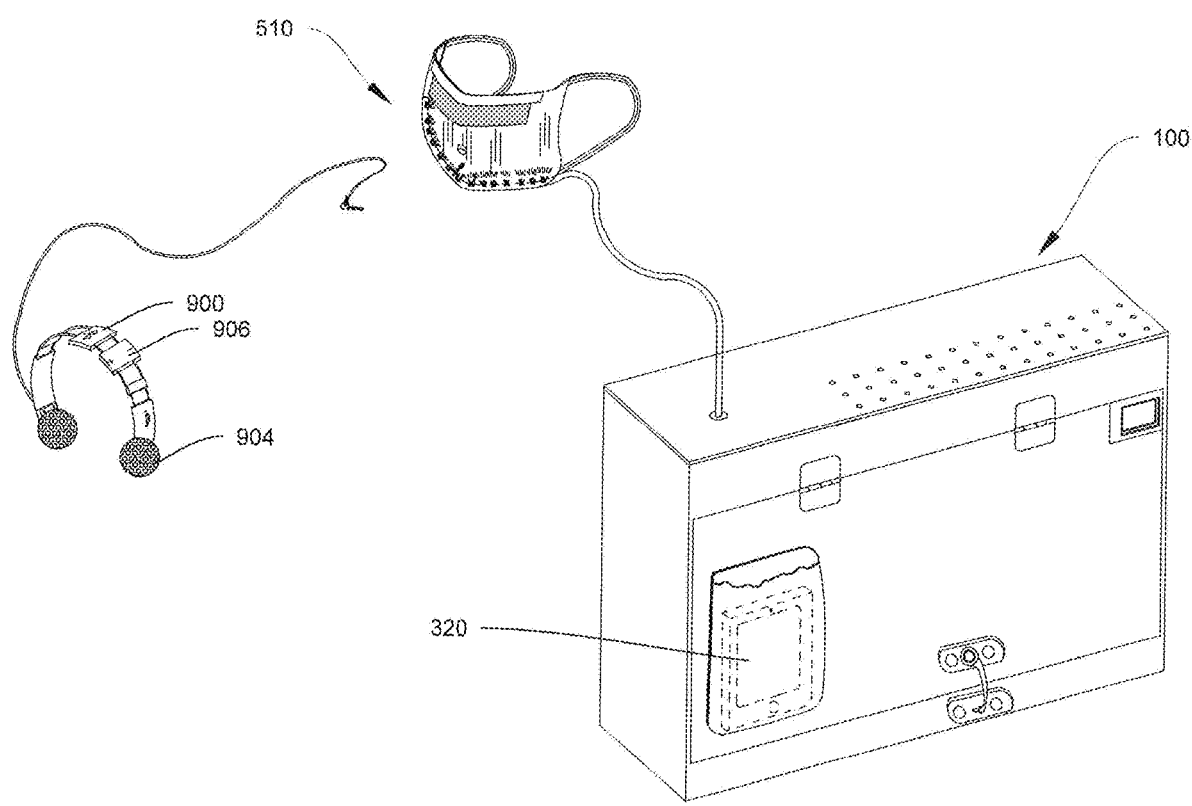
FIG. 8 illustrates an exemplary perspective view of a sealable half face mask connected to of the air purification and disinfection system integrated with speakers connectable to a mobile phone of a user, in accordance with an embodiment.

The air purification and disinfection apparatus 100 can include a controller embodied within a printed circuit board or PCB (not shown here). The PCB can also incorporate a wireless communication means to enable wireless communication, such as using Bluetooth, between the air purification and disinfection apparatus 100 and the mobile phone of the user. The phone can be configured with an application to control the apparatus 100. FIG. 8 shows an apparatus 100 attached to a mask 510 where the components of the apparatus 100 and its mask 510 can be coupled to a user interface such as a telephone or a PCB, Bluetooth 906, battery, volume control and speakers 904 connectable to the mask and controlled by the PCB 316 in the apparatus.

Figure 9:
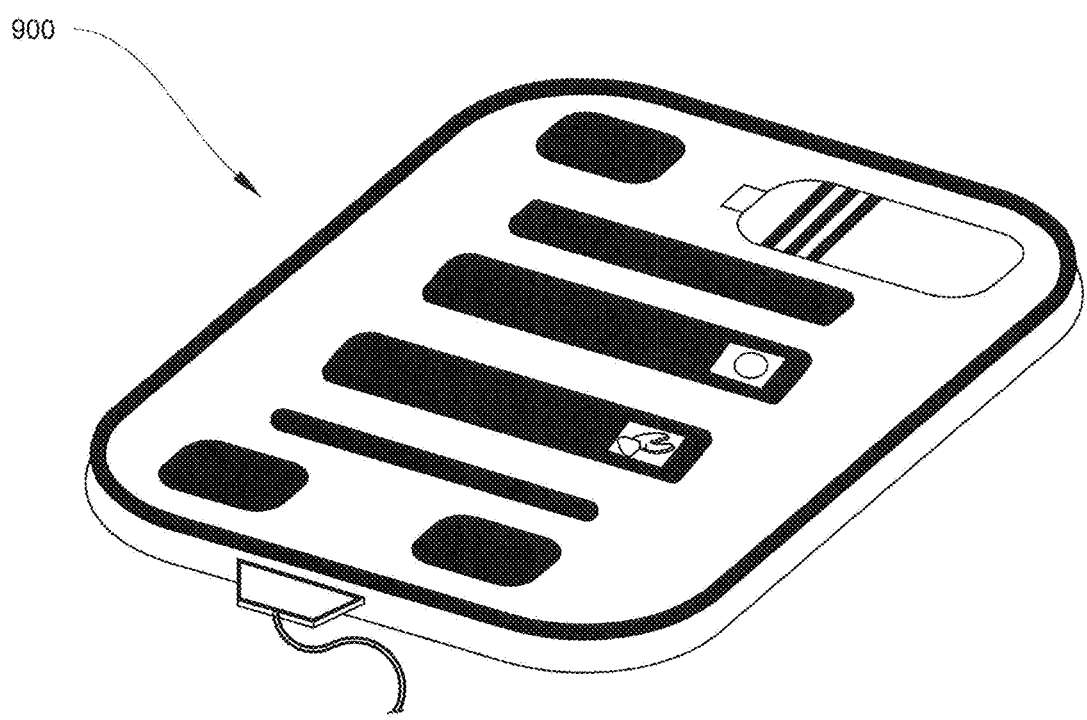
FIG. 9 shows a controller device displaying a software application to control operation of the air purification and disinfection system, in accordance with an embodiment.

FIG. 9 shows an exemplary screen display of a controller device 900. The screen display can include the status of the battery of the apparatus (i.e., the extent of charge on the battery), status of the controller device 900 being connected or not connected to the apparatus 100, a button to open the speaker functionality of the apparatus 100. The display can also include a button to open the airflow functionality of the apparatus 100, wherein by opening the airflow functionality, the controller device can be used to increase or reduce the airflow at which the apparatus 100 delivers purified, disinfected air to the mask 510. As can be understood the flow rate can be changed by changing speed of the pump 330 through the controller. The controller device 900 can also be used to control other functionalities, such as operating the LED lights 512 of the mask 510, turning ON or OFF the UV-C light sources 150, adding supplemental air or oxygen to the air stream, etc. Alternatively, a software program installed on a mobile device can be used to control the operation of the air purification and disinfection apparatus 100 using Wi-Fi or Bluetooth.

Figure 12:
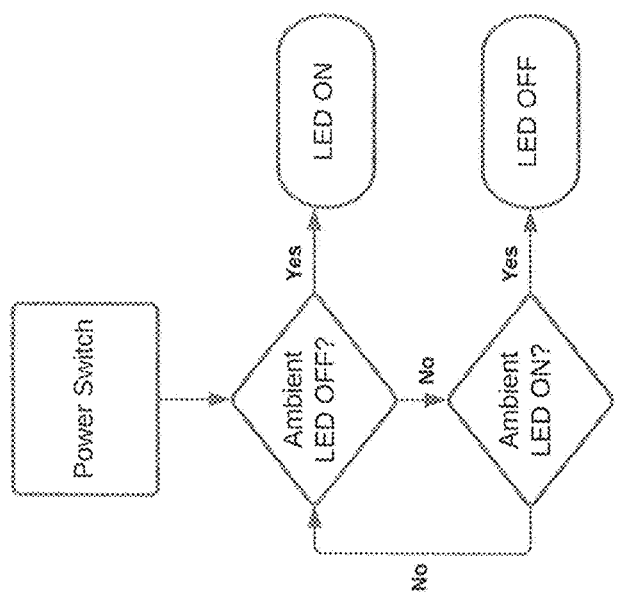

FIGS. 12 to 14 illustrate exemplary flow diagrams for functioning of the controller of the portable air disinfection system, wherein as shown in the flow diagrams the controller of the purification and disinfection apparatus 100 can carry out the functionalities of checking, charge level of the battery of the apparatus 100 and not turning the apparatus 100 to ON if the battery is not adequately charged; displaying the status of the battery; switching on the UV-C tubes 150; changing speed of the pump 330 based on inputs from the user; connecting the speakers and changing their volume based on input from the user; providing Bluetooth or wired connectivity to the speakers; and controlling the ambient LEDs 512 of the mask 510.

In an embodiment, as shown in FIG. 12, on actuation of a power switch of the apparatus 100 and/or the system, the controller can perform a pre-check operation before starting the apparatus 100, such as checking a charge level/voltage level of the battery. If the charge level of the battery is low then status of the battery can be displayed and the apparatus 100 is turned OFF. On the other hand, if it is found that the battery is charged above a threshold level, the controller can, after displaying the status of the battery, activate the apparatus 100 (i.e., the UV-C lamp and the air pump can be turned ON). The controller can further determine whether the apparatus 100 has been operating for a period of more than 5 minutes, if not, then the controller can check whether the Bluetooth of the mobile device is connected. Furthermore, after getting a positive Bluetooth connection, the controller can send commands associated with a change of airflow to the speed controller of the air pump to change the airflow based upon requirement.

In addition, when the controller finds that the apparatus 100 is operating for more than 5 minutes, the controller can reset the timer, and again check the charge level/voltage level of the battery of the apparatus 100. Thus, the controller is configured to check the battery status periodically, such as but not limited to every five minutes, to ensure that the battery is not drained.

Figure 11:
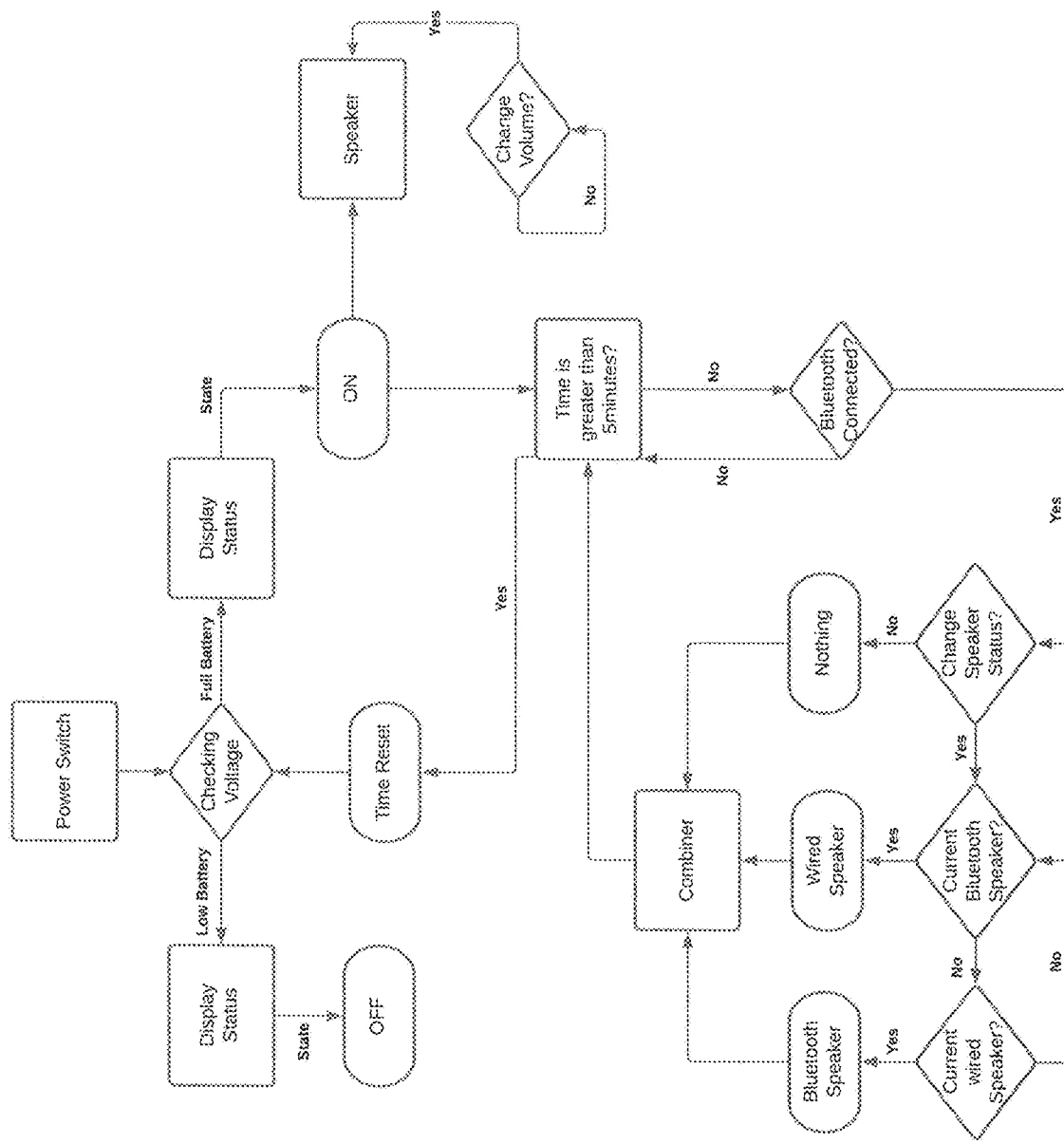

As shown in FIG. 11, when the battery is charged above the threshold level, the controller can activate/turn ON a speaker of the apparatus 100. In addition, the controller can change volume of the speaker based on requirement, after checking availability of the Bluetooth connectivity. If the Bluetooth is found connected, the controller can check status and/or change status of the speakers, such as Bluetooth speakers.

Figure 10:
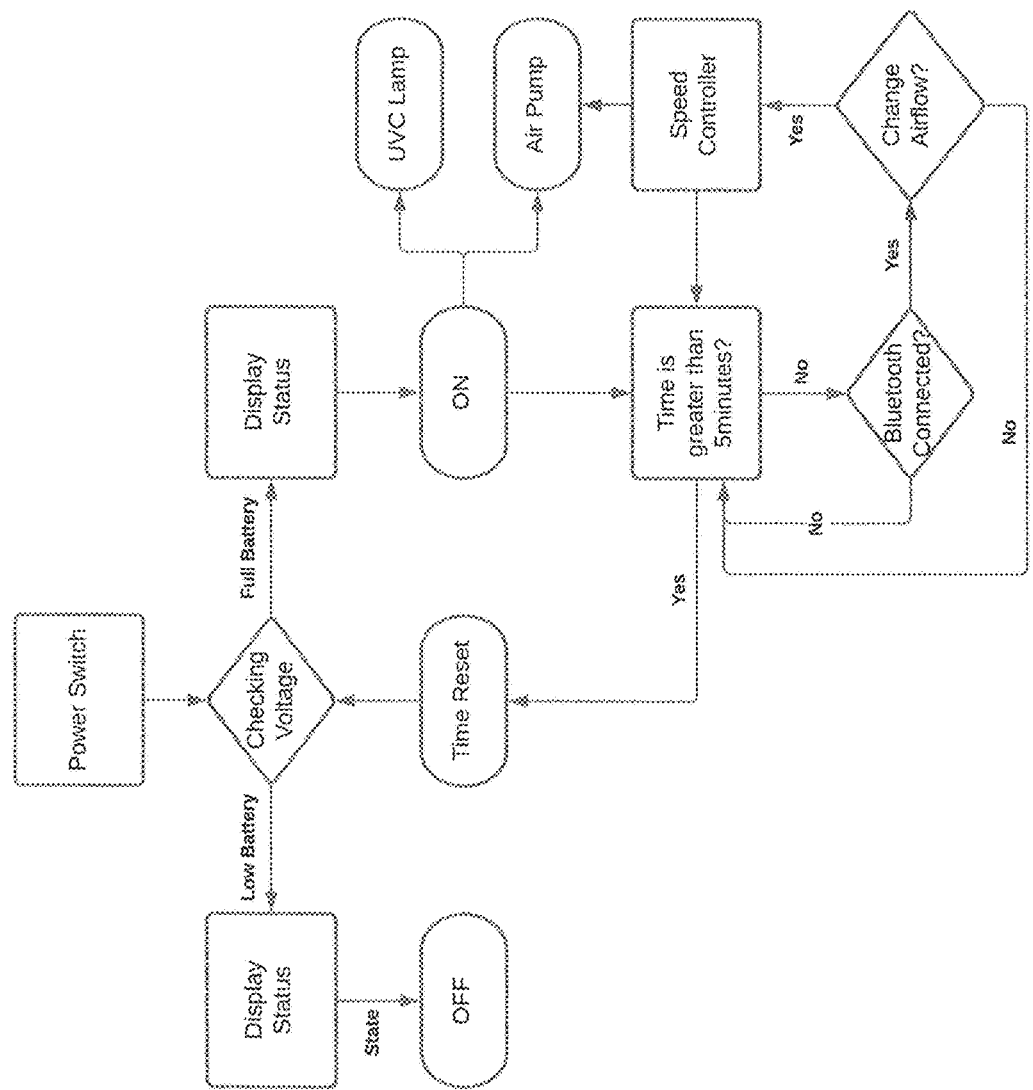
FIGS. 10-12 illustrate exemplary flow diagrams for functioning of the air purification and disinfection system, in accordance with embodiments of the present disclosure.

Further, as shown in FIG. 10, after actuation of the power switch of the apparatus 100 and/or the system, the controller can check whether the ambient LED is OFF. If it is found that the ambient was OFF, the controller can enable the functionality of turning ON the ambient LED. Further, if it is found that the ambient LED is not OFF, then the controller can further checks if the ambient LED is ON. If it is found that the ambient was ON, the controller can enable the functionality of turning the ambient lights.

This device can also include a controller that can be embodied in a printed circuit board (PCB) 295. The PCB can function as a conductor of the system. It can show the battery level, turn on or off the UV-C sources 150, control the fans 210, control the air flow into and out of the apparatus 100, and several other functions. The PCB 295 can also be used to sync the unit functions with a smart phone through an app and Bluetooth.

Methods of Use

A method of purifying and disinfecting an air source using the apparatus or system illustrated in FIG. 1 includes the steps of introducing the air source into the housing inlet 120 using an air mover to control the rate of air flow through the system; treating the air source in the housing 110 before sending the air source to the disinfection chambers enclosed in the inner box 140; exposing the air source in close proximity to the UV-C light sources 150 for a sufficient time period to disinfect the air source; sending the disinfected air source to the air distribution unit 170; and delivering the purified and disinfected air source to a user of the apparatus.

The air source may be treated or purified in the housing 110 using oxygen enhancement, HEPA filtration, 0.22 micron filtration, carbon dioxide absorption, activated charcoal absorption, or any combination thereof. The treated or purified air source is then introduced into the disinfection chambers enclosed in the inner box 140 where it is disinfected by exposing it to a sufficient dose of UV-C radiation to kill virulent bacteria, viruses, and other microorganisms.

Once the air source has been purified and disinfected, it is distributed to the user of the apparatus via a face mask or a ventilator.

While the foregoing describes various embodiments of the invention, additional embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

I claim:

1. A personal air purification and disinfection system comprising:
   (a) a housing having a housing inlet and a housing outlet, wherein the housing is opaque to UV-C light;
   (b) a pump in communication with the housing inlet and housing outlet, wherein the pump is configured to increase or decrease a rate of air flow in the housing;
   (c) an inner box containing multiple disinfection chambers embedded within the housing, each chamber containing a plurality of UV-C light sources, an air inlet and an air outlet;
   (d) a housing airflow pathway going from the housing inlet, winding through each of the multiple disinfection chambers from their air inlets to their air outlets, and exiting the housing through the housing outlet, wherein the air moves in a serpentine pathway as it moves from a first disinfection chamber to a second disinfection chamber;
   (e) a helical airflow diverter within each disinfection chamber, wherein the helical airflow diverter creates a helical path for the airflow pathway as the airflow pathway proceeds from the air inlet to the air outlet of each disinfection chamber; and
   (f) an air distribution unit in fluidic communication with the housing outlet and the housing inlet, wherein the air distribution unit comprises an airtight, sealable and transparent full face or a half face mask, and wherein the face mask delivers purified and disinfected air to a user of the system.

2. The personal air purification and disinfection system as claimed in claim 1, wherein the housing is in communication with a HEPA filter, a 0.22 micron filter, a carbon dioxide absorbent, an oxygen concentrator, an activated charcoal absorbent, or combinations thereof.

3. The personal air purification and disinfection system as claimed in claim 1, wherein the inner box contains a number of dividers oriented along a length or width thereof.

4. The personal air purification and disinfection system as claimed in claim 3, wherein each of the plurality of UV-C light sources are positioned within the disinfection chambers between the dividers.

5. The personal air purification and disinfection system as claimed in claim 4, wherein the dividers are staggered to provide a convoluted air passage in close proximity to the plurality of UV-C light sources.

6. The personal air purification and disinfection system as claimed in claim 1, wherein the air inlet and the air outlet of the disinfection chambers are located at opposing ends of the disinfection chambers.

7. The personal air purification and disinfection system as claimed in claim 6, wherein the air outlet of one disinfection chamber is positioned such that the air flow discharged from the air outlet will enter the air inlet of an adjacent disinfection chamber.

8. The personal air purification and disinfection system as claimed in claim 7, wherein an inside surface of the disinfection chambers comprises smooth and/or rough surfaces, and wherein the inside surface of the disinfection chambers is reflective and coated with titanium dioxide.

9. The personal air purification and disinfection system as claimed in claim 8, wherein the inside surface of the disinfection chambers is coated with a plurality of reflective and titanium dioxide coatings applied one on top of the other or applied in alternate up and down longitudinal strips extending the height of the inside surface of the disinfection chambers.

10. The personal air purification and disinfection system as claimed in claim 1, wherein each of the plurality of UV-C light sources is coupled to an upper and lower ballast.

11. The personal air purification and disinfection system as claimed in claim 1, wherein each of the plurality of UV-C light sources are LEDs and are coupled to an upper and a lower LED driver.

12. The personal air purification and disinfection system as claimed in claim 1, wherein the inner box contains a number of solid walled disinfection chambers, wherein each disinfection chamber has a top air passage and a bottom air passage and wherein the air travels a full length of the disinfection chambers in a zig-zag and serpentine pathway.

13. The personal air purification and disinfection system as claimed in claim 1, further comprising an inspection window.

14. The personal air purification and disinfection system as claimed in claim 1, wherein the face mask includes one or more ear loops, straps, belts, a light, a microphone, a speaker, a fan, a light, a selectably sealable elastomeric opening, a filter, an N95 strip with facility to open and close it, a metal nose clip, a battery, a collapsible tube, or combinations thereof.

15. The personal air purification and disinfection system as claimed in claim 14, wherein the housing outlet is coupled to a mask inlet port.

16. The personal air purification and disinfection system as claimed in claim 14, wherein a mask outlet port is coupled to the housing inlet.

17. The personal air purification and disinfection system as claimed in claim 1, further comprising a transport carrier.

18. The personal air purification and disinfection system as claimed in claim 17, wherein the housing is configured as the transport carrier.

19. The personal air purification and disinfection system as claimed in claim 18, wherein the transport carrier is selected from the group consisting of a backpack, a purse, a briefcase, a shoulder bag, a cervical collar, a hip pack, or a vest.

20. The personal air purification and disinfection system as claimed in claim 1, wherein oxygenated air from a ventilator enters the housing inlet and is purified and disinfected in the disinfection chambers and distributed to the user.

21. The personal air purification and disinfection system as claimed in claim 20, wherein exhaled air from the user is sent to the housing inlet and the purified and disinfected air exiting the system is sent to the ventilator before being distributed to the user.

22. The personal air purification and disinfection system as claimed in claim 1, wherein the personal air purification and disinfection system is incorporated into an airplane, a conference table, or a desk.

23. The personal air purification and disinfection system as claimed in claim 1, wherein substantially ambient air passes through a mixing valve where the ambient air can be enriched with oxygen after entering the housing inlet.

24. The personal air purification and disinfection system as claimed in claim 1, further comprising one or more fans positioned proximal to the housing inlet or the housing outlet.

25. The personal air purification and disinfection system as claimed in claim 1, wherein the plurality of UV-C light sources in the disinfection chambers include mercury lamps, fluorescent tubes, pulsed xenon lamps, excimer lamps, UV-C LEDs, or UV-C lasers.

26. The personal air purification and disinfection system as claimed in claim 1, wherein each of the plurality of UV-C light sources emits UV-C or far UV-C light/radiation.

27. The personal air purification and disinfection system as claimed in claim 1, further comprising a cooling unit in communication with each of the UV-C light sources.

28. The personal air purification and disinfection system as claimed in claim 1, wherein the housing is an extension of a ventilator with corresponding inlet and outlet tubes.

29. The personal air purification and disinfection system as claimed in claim 1, wherein the plurality of UV-C light sources in each disinfection chamber are light tubes mounted along the periphery of the helical airflow diverter between the helical airflow diverter and an inner surface of the disinfection chamber wall.

30. The personal air purification and disinfection system as claimed in claim 1, further comprising a tubing for delivering exhaled air from the face mask to a carbon dioxide absorption unit and then into the housing.

31. A personal air purification and disinfection system comprising:
    (a) a housing having a housing inlet and a housing outlet, wherein the housing is opaque to UV-C light;
    (b) a pump in communication with the housing inlet and housing outlet, wherein the pump is configured to increase or decrease a rate of airflow in the housing;
    (c) an inner box containing multiple disinfection chambers embedded within the housing, each chamber containing a plurality of UV-C light sources, an air inlet and an air outlet;
    (d) a housing airflow pathway going from the housing inlet, winding through each of the multiple disinfection chambers from their air inlets to their air outlets, and exiting the housing through the housing outlet, wherein the air moves in a serpentine pathway as it moves from a first disinfection chamber to a second disinfection chamber;
    (e) a helical airflow diverter within each disinfection chamber, wherein the helical airflow diverter creates a helical path for the airflow pathway as the airflow pathway proceeds from the air inlet to the air outlet of each disinfection chamber; and
    (f) an air distribution unit in fluidic communication with the housing outlet and the housing inlet, wherein the air distribution unit comprises an endotracheal tube in fluidic communication with a ventilator.

32. The personal air purification and disinfection system as claimed in claim 31, wherein the air distribution unit delivers purified and disinfected air to a user of the system via the endotracheal tube.

33. A method of purifying and disinfecting an air flow comprising:
    (a) providing the apparatus according to claim 1;
    (b) controlling a rate of flow that air moves through the apparatus;
    (c) moving the air through the housing and into the inner box containing multiple disinfection chamber;
    (d) exposing the air in close proximity to the UV-C light sources and the helical air flow diverters for a sufficient time period to disinfect the air;
    (e) sending the disinfected air to the air distribution unit; and
    (f) delivering the disinfected air to a user of the apparatus.

34. The method of claim 33, further comprising treating the air before entering the inner box using oxygen enhancement, HEPA filtration, 0.22 micron filtration, carbon dioxide absorption, or combinations thereof.

35. The method of claim 34, further comprising filtering the air through an activated carbon filter after exposing the air to the UV-C light sources.

36. The method of claim 33, wherein exhaled air of the user is included in the air entering the housing inlet and moving through the housing.

37. The method of claim 35, further comprising filtering the exhaled air of the user through a carbon dioxide filter before including the exhaled air into the air entering the housing inlet.

* * * * *